US012599329B2

(12) United States Patent
Verstreken et al.

(10) Patent No.: US 12,599,329 B2
(45) Date of Patent: Apr. 14, 2026

(54) SENSE AMPLIFIER FOR A PHYSIOLOGICAL SENSOR AND/OR OTHER SENSORS

(71) Applicant: INSPIRE MEDICAL SYSTEMS, INC., Golden Valley, MN (US)

(72) Inventors: Jan Verstreken, Rotselaar (BE); Tim Piessens, Bornem (BE); Heather Orser, Farmington, MN (US); David Dieken, Minneapolis, MN (US); John Rondoni, Golden Valley, MN (US); Timothy Denison, Oxford (GB)

(73) Assignee: Inspire Medical Systems, Inc., Golden Valley, MN (US)

( * ) Notice: Subject to any disclaimer, the term of this patent is extended or adjusted under 35 U.S.C. 154(b) by 553 days.

(21) Appl. No.: 18/008,226

(22) PCT Filed: Jun. 10, 2021

(86) PCT No.: PCT/US2021/036760
§ 371 (c)(1),
(2) Date: Dec. 5, 2022

(87) PCT Pub. No.: WO2021/257366
PCT Pub. Date: Dec. 23, 2021

(65) Prior Publication Data
US 2023/0172514 A1    Jun. 8, 2023

Related U.S. Application Data

(60) Provisional application No. 63/041,278, filed on Jun. 19, 2020.

(51) Int. Cl.
*H03F 3/45* (2006.01)
*A61B 5/30* (2021.01)
(Continued)

(52) U.S. Cl.
CPC .......... *A61B 5/30* (2021.01); *H03F 3/45479* (2013.01); *A61B 5/305* (2021.01); *A61B 5/31* (2021.01); *H03F 1/303* (2013.01)

(58) Field of Classification Search
CPC ......... H03F 2200/261; H03F 2200/264; H03F 2203/45138; H03F 2203/45526;
(Continued)

(56) References Cited

U.S. PATENT DOCUMENTS 5,944,680 A    8/1999  Christopherson et al.
8,718,783 B2   5/2014  Bolea et al.
(Continued)

FOREIGN PATENT DOCUMENTS

WO       2021257366 A1   12/2021

OTHER PUBLICATIONS

Schwartz et al., "Therapeutic Electrical Stimulation of the Hypoglossal Nerve in Obstructive Sleep Apnea", Arch Otolaryngol Head Neck Surg, vol. 127, Oct. 2001, pp. 1216-1223.
(Continued)

*Primary Examiner* — Andrea Lindgren Baltzell
*Assistant Examiner* — Khiem D Nguyen
(74) *Attorney, Agent, or Firm* — Dicke, Billig & Czaja, PLLC

(57)    ABSTRACT

A device includes a sensor signal input node and a high-pass filter stage. The high-pass filter stage includes an operational amplifier and a feedback integrator. The operational amplifier includes an input node coupled to the sensor signal input node. The feedback integrator is coupled between an output node of the operational amplifier and the input node of the operational amplifier to set a high-pass pole frequency of the high-pass filter stage.

21 Claims, 10 Drawing Sheets

(51) Int. Cl.

| | | |
|---|---|---|
| *A61B 5/305* | (2021.01) | |
| *A61B 5/31* | (2021.01) | |
| *H03F 1/30* | (2006.01) | |

(58) Field of Classification Search

CPC . H03F 2203/45534; H03F 2203/45591; H03F 3/181; H03F 3/38; H03F 3/45475; H03F 3/45928; A61B 5/30; A61B 5/305; A61B 5/31; A61B 5/304; A61B 5/307; A61B 5/308; A61B 5/311; A61B 5/313; A61N 1/36125; A61N 1/362

USPC ............................................. 330/9, 252–261

See application file for complete search history.

(56) References Cited

U.S. PATENT DOCUMENTS

| | | | |
|---|---|---|---|
| 8,938,299 | B2 | 1/2015 | Christopherson et al. |
| 9,084,551 | B2 | 7/2015 | Brunnett et al. |
| 9,381,358 | B2 | 7/2016 | Ternes et al. |
| 9,486,628 | B2 | 11/2016 | Christopherson et al. |
| 9,566,015 | B2 | 2/2017 | Murphy et al. |
| 9,889,299 | B2 | 2/2018 | Ni et al. |
| 10,105,538 | B2 | 10/2018 | Bolea et al. |
| 10,632,306 | B2 | 4/2020 | Bolea et al. |
| RE48,024 | E | 6/2020 | Bolea et al. |
| 10,758,164 | B2 | 9/2020 | Derkx |
| 10,898,709 | B2 | 1/2021 | Wagner et al. |
| 11,123,023 | B2 | 9/2021 | Babaeizadeh |
| 11,324,950 | B2 | 5/2022 | Dieken et al. |
| 2002/0171773 | A1* | 11/2002 | Gower ................ H03F 3/45197 348/E5.073 |
| 2011/0046499 | A1 | 2/2011 | Klewer et al. |
| 2011/0066064 | A1 | 3/2011 | Jangle et al. |
| 2015/0164380 | A1 | 6/2015 | O'Dwyer et al. |
| 2017/0230019 | A1 | 8/2017 | Chandrakumar et al. |
| 2019/0133499 | A1 | 5/2019 | Auerbach |
| 2019/0175026 | A1 | 6/2019 | Verzal et al. |
| 2020/0030610 | A1* | 1/2020 | Stanslaski .......... A61N 1/36178 |
| 2020/0099352 | A1* | 3/2020 | Chandrakumar ........ A61B 5/24 |
| 2020/0147376 | A1 | 5/2020 | Dieken et al. |
| 2020/0254249 | A1 | 8/2020 | Rondoni et al. |
| 2020/0391028 | A1 | 12/2020 | Verzal et al. |
| 2021/0169378 | A1 | 6/2021 | Gerard et al. |
| 2022/0000435 | A1 | 1/2022 | Babaeizadeh |
| 2022/0095952 | A1 | 3/2022 | Schipper et al. |
| 2022/0111201 | A1 | 4/2022 | Verzal et al. |
| 2022/0134103 | A1 | 5/2022 | Elyahoodayan et al. |
| 2022/0134104 | A1 | 5/2022 | Elyahoodayan et al. |

OTHER PUBLICATIONS

Fan et al., "A 2.1 μW area-efficient capacitively-coupled chopper instrumentation amplifier for ECG applications in 65 mm CMOS", 2010 IEEE Asian Solid-State Circuits Conference, Nov. 8, 2010, pp. 1-4.

Lee et al., "A Multi-Functional Physiological Hybrid-Sensing E-Skin Integrated Interface for Wearable IoT Applications", IEEE Trans Biomed Circuits Syst., vol. 13, No. 6, Dec. 1, 2019, pp. 1535-1544.

\* cited by examiner

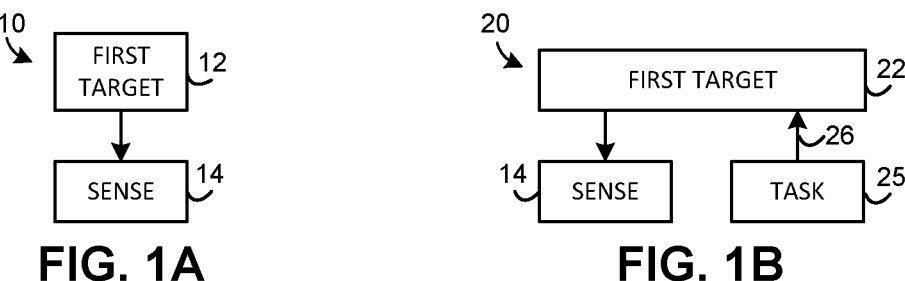
FIG. 1A          FIG. 1B
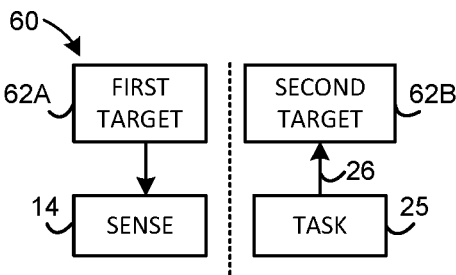
FIG. 1C
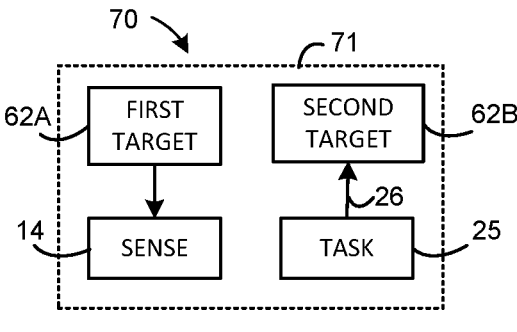
FIG. 1D

700 —

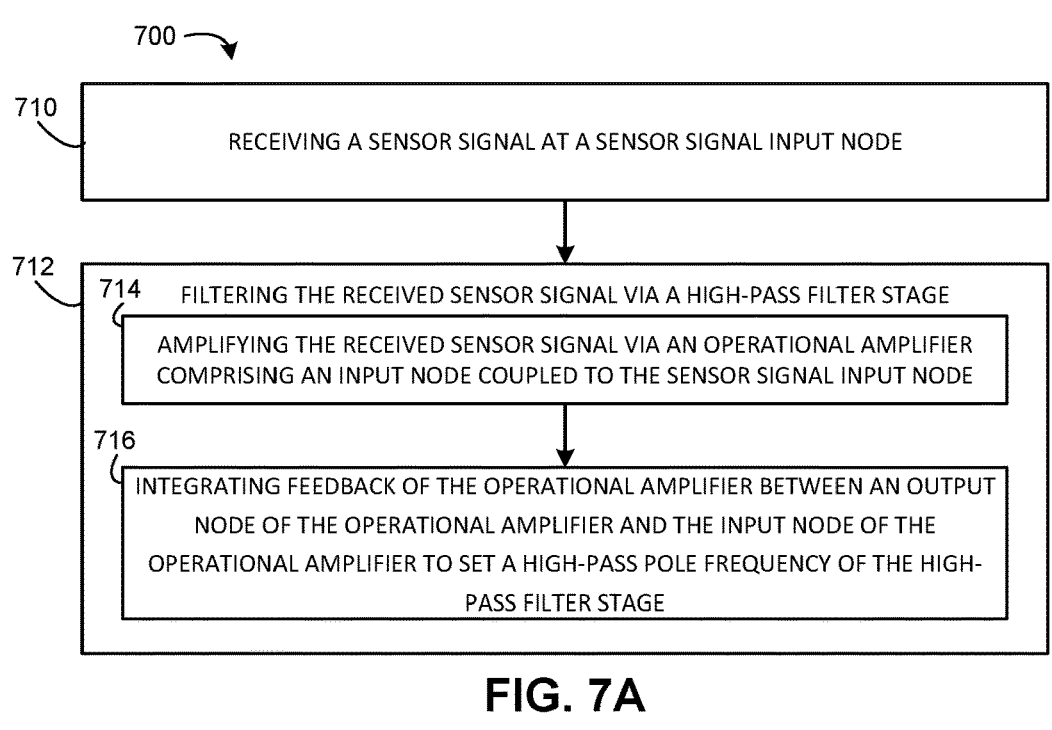

710 — RECEIVING A SENSOR SIGNAL AT A SENSOR SIGNAL INPUT NODE

712

714 FILTERING THE RECEIVED SENSOR SIGNAL VIA A HIGH-PASS FILTER STAGE

AMPLIFYING THE RECEIVED SENSOR SIGNAL VIA AN OPERATIONAL AMPLIFIER COMPRISING AN INPUT NODE COUPLED TO THE SENSOR SIGNAL INPUT NODE

716

INTEGRATING FEEDBACK OF THE OPERATIONAL AMPLIFIER BETWEEN AN OUTPUT NODE OF THE OPERATIONAL AMPLIFIER AND THE INPUT NODE OF THE OPERATIONAL AMPLIFIER TO SET A HIGH-PASS POLE FREQUENCY OF THE HIGH-PASS FILTER STAGE

FIG. 7A

718 — SELECTIVELY BLANKING A TASK SIGNAL TO PREVENT THE TASK SIGNAL FROM BEING INPUT TO THE OPERATIONAL AMPLIFIER

FIG. 7B

720 — SELECTIVELY COUPLING THE SENSOR SIGNAL INPUT NODE TO ONE OF A PLURALITY OF ELECTRODE NODES IN RESPONSE TO AN ELECTRODE SELECTION SIGNAL

FIG. 7C

722 — AMPLIFYING, VIA A FIRST PROGRAMMABLE GAIN AMPLIFIER STAGE, THE FILTERED SENSOR SIGNAL ON THE OUTPUT NODE OF THE OPERATIONAL AMPLIFIER

FIG. 7D

724 — AMPLIFYING, VIA A SECOND PROGRAMMABLE GAIN AMPLIFIER STAGE, THE FILTERED AND AMPLIFIED SENSOR SIGNAL ON AN OUTPUT NODE OF THE FIRST PROGRAMMABLE GAIN AMPLIFIER STAGE

FIG. 7E

726 — CONVERTING THE FILTERED AND AMPLIFIED SENSOR SIGNAL ON AN OUTPUT NODE OF THE SECOND PROGRAMMABLE GAIN AMPLIFIER STAGE TO A DIGITAL VALUE

FIG. 7F

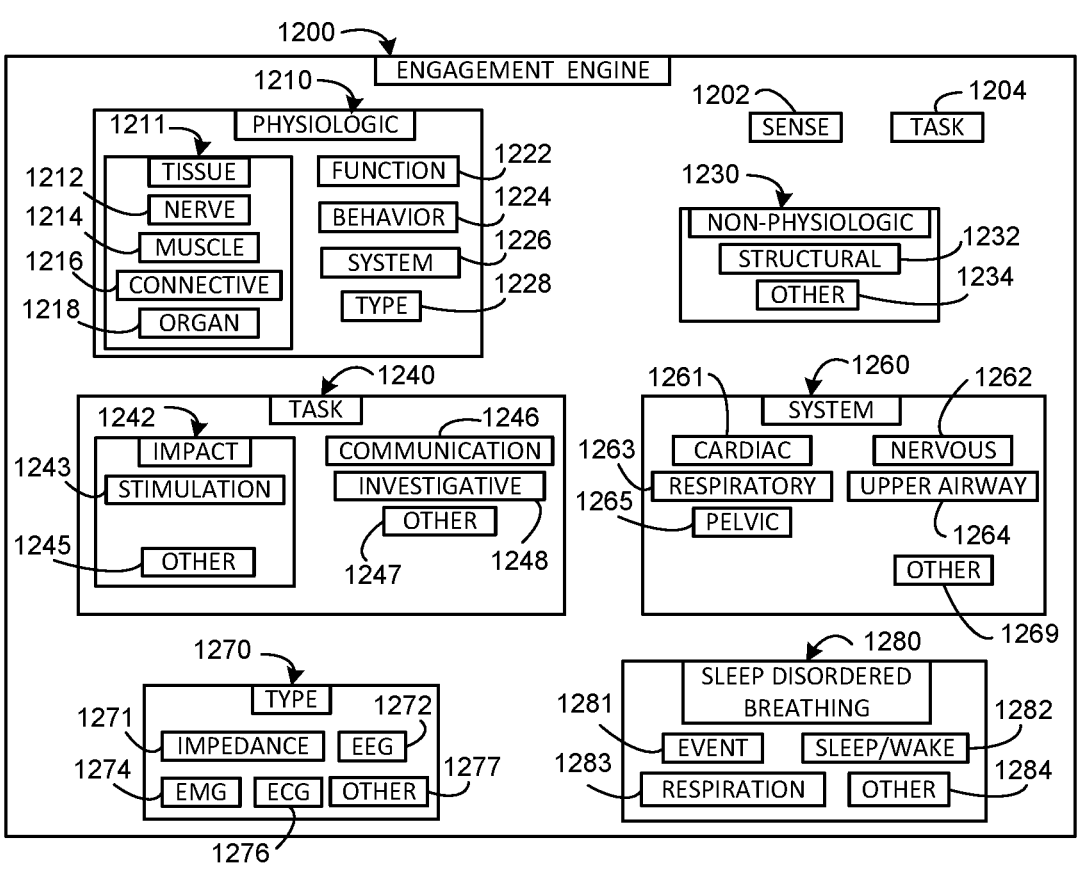
FIG. 9
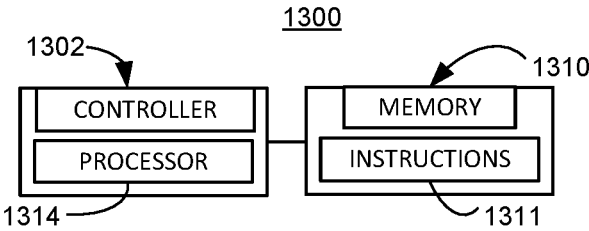
FIG. 10A
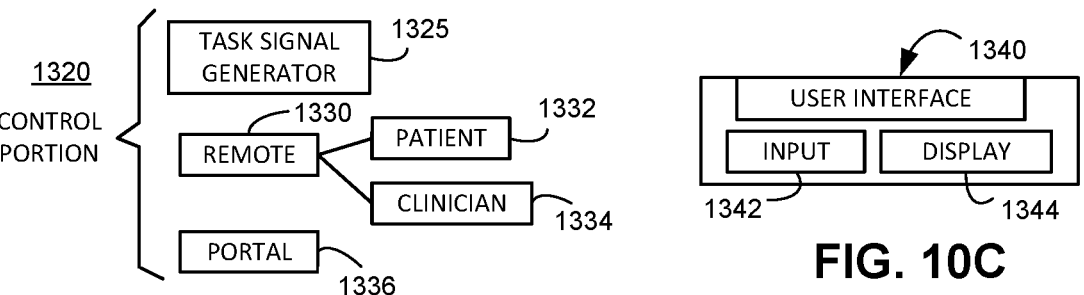
FIG. 10B
FIG. 10C

1400

1410 — SENSING, VIA A FIRST SIGNAL, A FIRST PARAMETER IN RELATION TO A FIRST TARGET

1412 — FILTERING AND AMPLIFYING, VIA A SENSE AMPLIFIER, THE SENSED FIRST SIGNAL

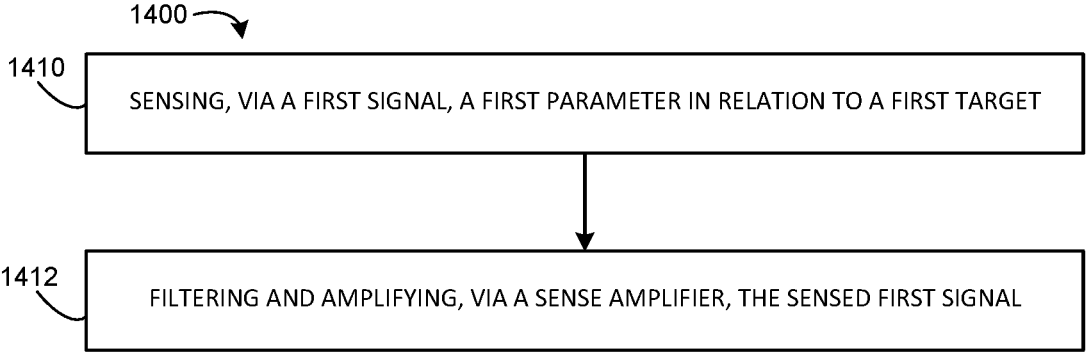

FIG. 11A

1422 — APPLYING, IN A SAME TIME FRAME AS THE SENSING, A TASK SIGNAL IN RELATION TO A SECOND TARGET

1424 — BLOCKING RECEPTION OF THE TASK SIGNAL AT, AND VIA, THE SENSE AMPLIFIER DURING THE APPLICATION OF THE TASK SIGNAL

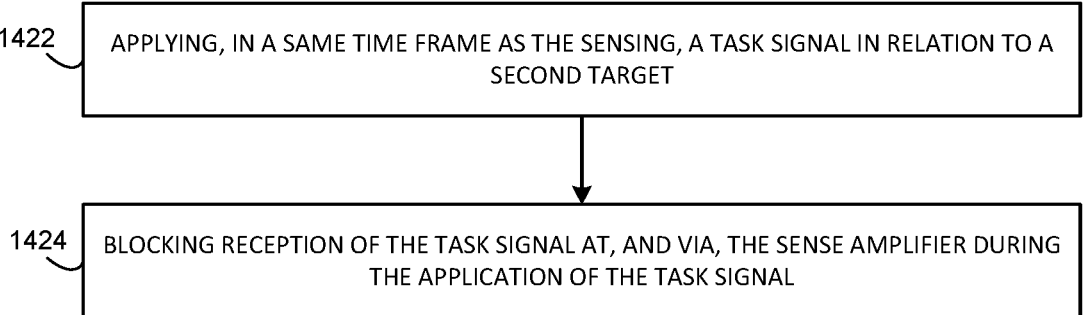

FIG. 11B

1430 — TRIGGERING THE BLOCKING, VIA A TASK ENGINE, DURING A TASK PERIOD IN WHICH THE TASK ENGINE CAUSES APPLICATION OF THE TASK SIGNAL

FIG. 11C

SENSE AMPLIFIER FOR A PHYSIOLOGICAL SENSOR AND/OR OTHER SENSORS

CROSS-REFERENCE TO RELATED APPLICATIONS

This 35 U.S.C. § 371 National Phase application claims priority to International Application No. PCT/US2021/036760, filed Jun. 10, 2021, which claims the benefit of U.S. Provisional Patent Application No. 63/041,278, filed Jun. 19, 2020; which are both incorporated herein by reference in their entirety.

BACKGROUND

Sensors may be used to sense a wide variety of phenomenon, some of which may produce sensing signals with low amplitudes. Among other devices including sensors, implantable medical devices may include sensors to sense physiologic signals, such as signals from the heart, lungs, nerves, etc.

BRIEF DESCRIPTION OF THE DRAWINGS

FIGS. 1A-1D are a series of block diagrams schematically representing example arrangements including sensing elements and/or task engines.

FIGS. 7A-7F are a series of flow diagrams schematically representing an example method.

FIG. 9 is a block diagram schematically representing an example engagement engine.

FIG. 10A is a block diagram schematically representing an example control portion.

FIG. 10B is a block diagram schematically representing various example control portion arrangements.

FIG. 10C is a block diagram schematically representing an example user interface.

FIGS. 11A-11C are a series of flow diagrams schematically representing example methods relating to sensing and/or applying a task signal.

DETAILED DESCRIPTION

Figure 2A:
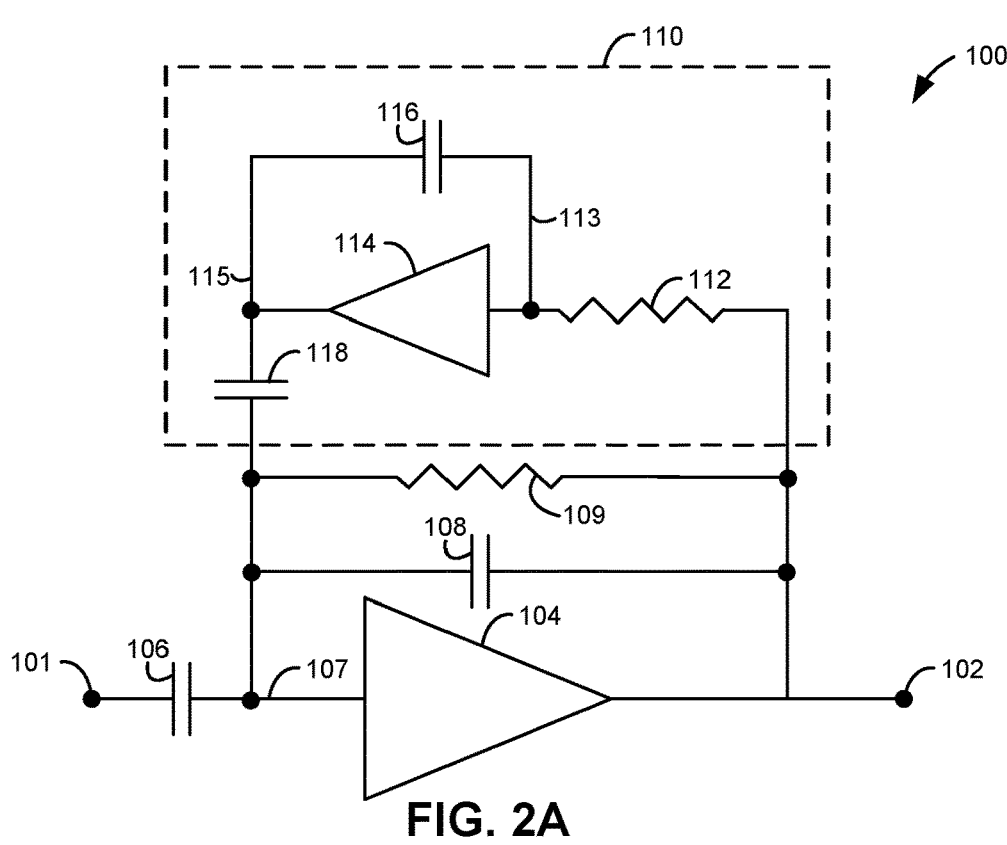
FIG. 2A is a schematic diagram illustrating one example of a device including a high-pass filter stage.

In the following detailed description, reference is made to the accompanying drawings which form a part hereof, and in which is shown by way of illustration specific examples in which the disclosure may be practiced. It is to be understood that other examples may be utilized and structural or logical changes may be made without departing from the scope of the present disclosure. The following detailed description, therefore, is not to be taken in a limiting sense. It is to be understood that features of the various examples described herein may be combined, in part or whole, with each other, unless specifically noted otherwise.

At least some examples of the present disclosure provide for sensing. In some examples, such sensing may be implemented via a sense amplifier which may enable sensing very small local signals (e.g., less than about 1 mV). In some such examples, the sensing signal may comprise a frequency on the order of 0 to 500 Hz.

In some examples, it may be desirable for a device to sense such signals in the presence of a task signal. For instance, to sense signals in the presence of a task signal, a sense amplifier may accommodate a large dynamic range of common mode signals (e.g., greater than about 10 mV) while maintaining the ability to sense very small local signals (e.g., less than about 1 mV) in the presence of significant noise in the active components using very little power (e.g., less than about 5 µW). A variety of sense amplifiers exist, however, many of these sense amplifiers struggle to maintain appropriate sensing in the presence of large common mode signals.

In some examples, the above-noted sensing signals may comprise sensing biological signals (e.g., physiologic signals). Meanwhile, in some examples, the above-noted task signal may comprise an impact signal to provide some impact to biological tissue. In some examples, an impact signal may comprise a stimulation signal to stimulate biological tissue, may comprise an electrosurgical signal to cut, ablate, or cauterize tissue, or may comprise a magnetic signal to stimulate cranial tissue, and so on.

With this in mind, it may be desirable in some examples for an implantable medical device (IMD) to sense a variety of biological signals in a patient in the presence of an example task signal, which may comprise an impact signal (e.g., therapeutic electrical stimulation pulses) to tissue within a patient. To sense biological signals in the presence of stimulation, a sense amplifier should accommodate a large dynamic range of common mode signals (e.g., greater than about 10 mV) while maintaining the ability to sense very small local signals (e.g., less than about 1 mV) in the presence of significant noise in the active components using very little power (e.g., less than about 5 µW). A variety of sense amplifiers have been designed for sensing in a patient, however, many of these sense amplifiers struggle to maintain appropriate sensing in the presence of large common mode signals.

Accordingly, at least some examples disclosed herein provide a sense amplifier including common mode feedback circuitry to account for large swings due to the presence of a task signal (e.g., an impact signal, such as stimulation) that impacts the signal of interest. The sense amplifier disclosed herein also synchronizes the sensing times with the task circuitry to ensure measurements are performed at a desired point in time to allow signal settling. In one example, the sense amplifier disclosed herein includes three amplification stages configured to provide a total amplification of up to about 40,000 with a bandwidth of about 500 Hz and noise of about 1 µArms between about 0.1 Hz and about 15 Hz. The electrodes coupled to the disclosed sense amplifier are subject to significant aggressors, such as but not limited to a task signal, which may saturate the sense amplifier. Such aggressors might otherwise interfere with accurate sensing (of phenomenon having a small amplitude and/or other fine characteristics) in the absence of the common mode feed-back circuitry, which ensures appropriate operation of the example sense amplifier.

Among other biological signals, in some examples a sense amplifier may be implemented near and/or during stimulation within the patient's body to facilitate monitoring cardiac phenomenon (e.g., heart rate, other), muscle activity, nerve activity, and the like. For instance, the sense amplifier may be used to monitor cardiac behavior, such as via electrocardiographic (ECG) signals. The sense amplifier may also be used to monitor cardiac parameters of patients via a respiratory rate and/or a heart rate. In some instances, such data can be used to approximate electrocardiogram information, such as a QRS complex. In some instances, the detected heart rate is used to identify a relative degree of organized heart rate variability, in which organized heart rate variability may enable detecting apneas or other sleep disordered breathing events, which may enable evaluating efficacy of sleep disordered breathing. In some instances, the detected heart rate is used to identify characteristics of organized heart rate variability, in which organized heart rate variability may enable detecting sleep stage (e.g., N1, N2, N3, REM). In some instances, the detected heart rate is used to identify disorganized heart rate variability, which may enable detecting cardiac disorders, such as arrhythmias (e.g., atrial fibrillation, ventricular tachycardia, etc.), for which cardiac intervention (e.g., ablation, drug therapy, etc.) may be appropriate.

The sense amplifier also may be used to assess muscle activity (e.g., contraction, tone, etc.) indicative of stimulation, such as via electromyography (EMG). The sense amplifier also may facilitate assessing nerve activity such as, but not limited to nerve activity indicative of tongue movement. In some examples, assessing nerve activity via the example sense amplifier may comprise sensing electroencephalographic (EEG) signals. In some examples, a combination of such signals (e.g., cardiac, muscle, nerve) may be sensed and in some examples, combined with accelerometer data to make determinations regarding various physiologic conditions, behaviors, etc. At least some of the sensing of such cardiac, muscle, and/or nerve activity may be used in monitoring and/or therapy of sleep disordered breathing (SDB), which may comprise various forms of sleep apnea, including obstructive, central, and/or multiple-type.

In some examples, the sense amplifier also may be implemented favorably in situations lacking cotemporaneous stimulation of nerves and/or muscles within a patient or in situations lacking any stimulation of nerves and/or muscles.

In some examples, more generally speaking, the sense amplifier may comprise a power efficient amplifier which may be employed to sense a wide variety of phenomenon, which may comprise physiologic phenomenon or other phenomenon. Such sensing may be cotemporaneous with stimulation or may be without contemporaneous stimulation. In some such examples, the sense amplifier may be used to sense phenomenon involving small impedances.

These examples, and additional examples, are described below in association with FIGS. 1A-12C.

FIGS. 1A-1D schematically represent various example arrangements in which a sensing element and/or task element may be situated relative to each other, and relative to targets. These example arrangements illustrate at least some environments in which various sense amplifiers, blanking arrangements (e.g., switches), multiplexers, etc. of FIGS. 2A-6 may be implemented.

With this in mind, FIG. 1A schematically represents an example arrangement 10 including an example device and/or example method of sensing, via a sensing element 14 and a first target 12. As previously noted, the sensing element 14 may comprise, or may be used with, a sense amplifier which may enable sensing very small local signals (e.g., less than about 1 mV). In some such examples, the sensing signal may comprise a frequency on the order of 0 to 500 Hz. In some examples, the active components associated with the sensing element 14 may use very little power (e.g., less than about 5 μW).

The sensing element 14 may comprise a wide variety of features to sense information. Among other potential features, in some examples the sensing element 14 may comprise at least two spaced apart electrodes by which a sensing signal may be obtained. At least some example electrode arrangements are further described later in association with at least FIGS. 8A-8E. Moreover, the sensing element 14 may be used to sense a wide variety of phenomenon, as further described later in association with at least FIG. 9.

FIG. 1B schematically represents an example arrangement 20 including an example device and/or example method of sensing, via a sensing element 14, a first target 22, and a task element 25 to apply a task signal 26 relative to the same first target 22. The task signal 26 may comprise a variety of types of signals such as, but not limited to, a stimulation signal or other impact signal. In at least this context, the term "impact" refers to a task signal having some effect on a target, and does not refer to an impact resulting from physical movement such as from two objects colliding. At least some example task signals are described further in association with at least FIG. 9.

With further reference to FIG. 1B, in some instances, features of the task signal 26 might otherwise overwhelm various filtering and processing circuitry of (or associated with) the sensing element 14, but for certain features of the example sense amplifiers, etc. as described in at least examples in FIGS. 2A-6 of the present disclosure.

FIG. 1C schematically represents an example arrangement 60 in which the sensing element 14 is to sense a first target 62A and the task element 25 is to apply a task signal to a second target 62B, with the second target 62B being separate from the first target 62A. In some such examples, a task signal 26 applied via the task element 25 to the second target 62B does not directly affect the first target 62A, but the task signal 26 may affect the sensing element 14. However, as noted above, and as explained later in association with at least some examples in FIGS. 2A-6, the sensing element 14 may comprise certain features which may lessen or neutralize the effects of the task signal 26 on the sensing element 14.

FIG. 1D schematically represents an example arrangement 70 comprising at least some of substantially the same features and attributes as example arrangement 60 in FIG. 1C, except with the respective first and second targets 62A, 62B being related in some manner (as represented by dashed box 71) by which application of the task signal (via task element 25) to the second target 62B may directly affect the first target 62A.

With these example sensing arrangements in mind, FIGS. 2A-6 provide various example implementations to enhance sensing and/or to mitigate the effects of a task signal (e.g., 26) on such sensing.

FIG. 2A is a schematic diagram illustrating one example of a device including a high-pass filter stage 100. In some examples, the high-pass filter stage 100 may be part of sensing element 14 of FIGS. 1A-1D. The device includes a sensor signal input node 101 and an output node 102. High-pass filter stage 100 includes an operational amplifier 104, in input capacitor 106, a feedback capacitor 108, and a resistor 109. High-pass filter stage 100 also includes a feedback integrator 110. Feedback integrator 110 includes an input resistor 112, a feedback amplifier 114, a feedback capacitor 116, and an output capacitor 118. In one example, input resistor 112 is a pseudo resistor. By using a pseudo resistor, area used to implement the resistor may be reduced.

The sensor signal input node 101 is electrically coupled to one side of the input capacitor 106. The other side of the input capacitor 106 is electrically coupled to the input of the operational amplifier 104, one side of the feedback capacitor 108, one side of the resistor 109, and one side of the output capacitor 118 through an input node 107 of the operational amplifier 104. The output of the operational amplifier 104 is electrically coupled to the other side of the feedback capacitor 108, the other side of the resistor 109, and one side of the input resistor 112 through the output node 102. The other side of the input resistor 112 is electrically coupled to the input of feedback amplifier 114 and one side of feedback capacitor 116 through a signal path 113. The output of feedback amplifier 114 is electrically coupled to the other side of feedback capacitor 116 and the other side of output capacitor 118 through a signal path 115.

The gain of high-pass filter stage 100 is set based on the input capacitor 106 and the feedback capacitor 108. In one example, the input capacitor 106 has a capacitance (e.g., 40 pF) 100 times the capacitance (e.g., 400 fF) of feedback capacitor 108, such that high-pass filter stage 100 has a gain of about 100. In other examples, high-pass filter stage 100 may be configured to have another suitable gain.

The feedback integrator 110 sets a high-pass pole frequency of the high-pass filter stage 100. The frequency behavior of the feedback integrator is given by:

$$\frac{1}{2\pi \cdot R_{in} \cdot C_{fb} \cdot f}$$

where:

R$_{in}$ is the resistance of input resistor 112;

C$_{fb}$ is the capacitance of feedback capacitor 116; and f is the frequency.

The output voltage of the feedback amplifier 114 is connected via output capacitor 118 to the input node 107 of the operational amplifier 104 to convert this voltage to a current. On input node 107, the current from feedback integrator 110 is summed with the input current from input capacitor 106. In one example, the capacitance of the output capacitor 118 is selected to be one-tenth the capacitance of the input capacitor 106. In this example, therefore, a 100 mV differential swing at the sensor input node 101 will be cancelled by integrating 1 V on output capacitor 118. The high-pass pole frequency can be calculated by multiplying the zero-dB point of the feedback integrator 110 and the loop gain of the feedback integrator 110 feedback path. This gain is defined by the output capacitor 118 and the feedback capacitor 116. In one example, this gain is 10, and the high-pass pole frequency is thus:

$$\frac{1}{2\pi \cdot R_{in} \cdot C_{fb}}$$

The feedback integrator 110 also eliminates the offset of operational amplifier 104 as the offset of operational amplifier 104 is indistinguishable from a DC signal for the feedback integrator 110. In one example, feedback integrator 110 is configured to have a 0.3 Hz high-pass pole frequency. The resistor 109 in parallel with the feedback capacitor 108 prevents saturation of the feedback amplifier 114 by providing a DC path for input node 107.

Figure 2B:
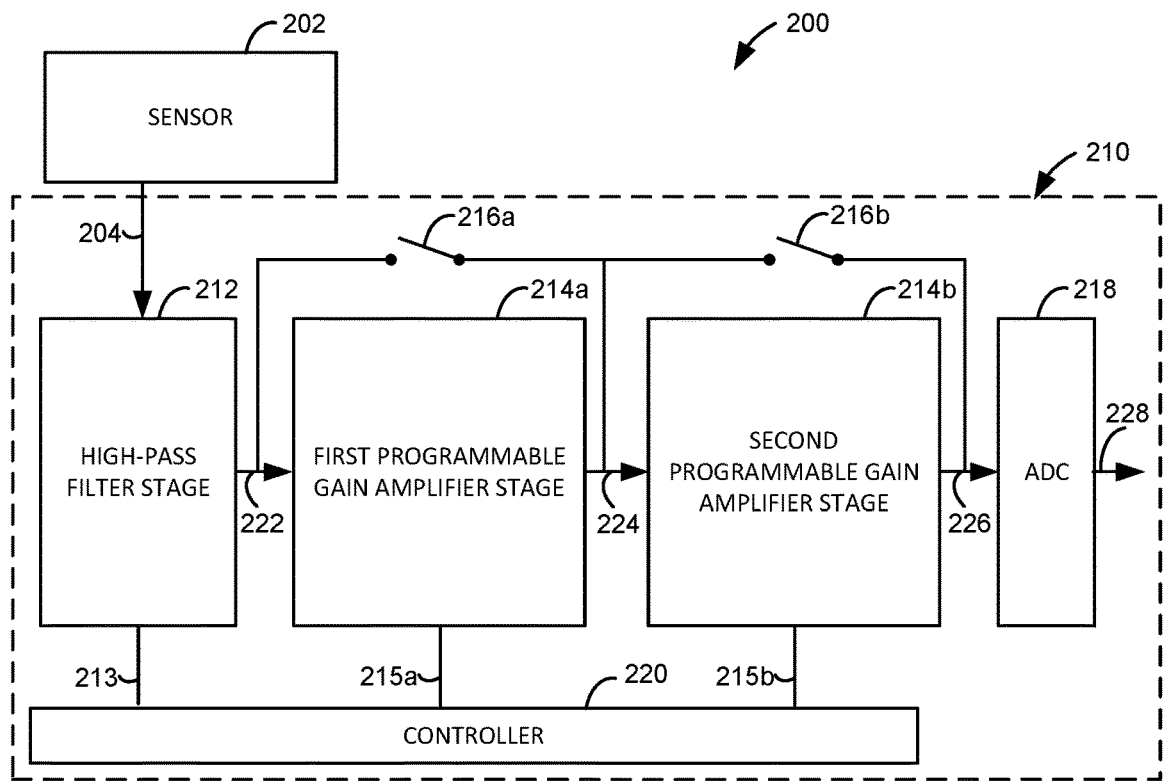
FIG. 2B is a block diagram illustrating one example of a device including a sensor and a sense amplifier.

FIG. 2B is a block diagram illustrating one example of a device 200 including a sensor 202 and a sense amplifier 210. In some examples, the sensor 202 comprises a physiologic sensor and/or another type of sensor, as described in association with at least FIGS. 1A-1F, FIGS. 8A-8F, and/or FIG. 9. In some examples, device 200 may be part of sensing element 14 of FIGS. 1A-1D.

As shown in FIG. 2B, in some examples the sense amplifier 210 includes a high-pass filter stage 212, a first programmable gain amplifier stage 214a, a first bypass switch 216a, a second programmable gain amplifier stage 214b, a second bypass switch 216b, an analog to digital converter 218, and a controller 220. An output of the sensor 202 is electrically coupled to a sensor input of the high-pass filter stage 212 through a signal path 204. An output of the high-pass filter stage 212 is electrically coupled to an input of the first programmable gain amplifier stage 214a and one side of the first bypass switch 216a through a signal path 222. The output of first programmable gain amplifier stage 214a and the other side of the first bypass switch 216a is electrically coupled to an input of the second programmable gain amplifier stage 214b and one side of the second bypass switch 216b through a signal path 224. Thus, first bypass switch 216a is coupled in parallel with the first programmable gain amplifier stage 214a. The output of second programmable gain amplifier stage 214b and the other side of the second bypass switch 216b is electrically coupled to an input of the analog to digital converter 218 through a signal path 226. Thus, second bypass switch 216b is coupled in parallel with the second programmable gain amplifier stage 214b. An output of analog to digital converter 218 is electrically coupled to a signal path 228. Controller 220 is electrically coupled to a control input of high-pass filter stage 212 through a control signal path 213, a control input of first programmable gain amplifier stage 214a through a control signal path 215a, and a control input of second programmable gain amplifier stage 214b through a control signal path 215b.

In some examples, the sensor 202 may comprise at least some of substantially the same features and attributes as the sensing element(s) described in association with at least FIGS. 1A-1D, FIGS. 8A-8F, and/or FIG. 9. In some such examples, the sensor 202 may comprise a physiologic sensor, which may be configured to sense a signal from the heart, lungs, nerves, or other suitable tissues of a patient, as described throughout the various examples of FIGS. 1A-1F, 8A-8F, and/or 9.

In one example, sensor 202 may include two electrodes (i.e., a positive electrode and a negative electrode) to sense a differential signal. At least some example implementations of multiple electrode configurations are described later in association with at least FIGS. 8A-8F and/or 9.

In some examples, high-pass filter stage 212 in FIG. 2B may include high-pass filter stage 100 previously described and illustrated with reference to FIG. 2A or high-pass filter stage 300 or 500 to be described below with reference to FIGS. 3 and 5, respectively.

With further reference to FIG. 2B, in one example, high-pass filter stage 212 is a differential high-pass filter stage to high-pass filter and amplify a differential sensor signal from the sensor 202. The first programmable gain amplifier stage 214a may further amplify the sensor signal from high-pass filter stage 212. First programmable gain amplifier stage 214a may include programmable gain amplifier stage 400 or 600 to be described below with reference to FIGS. 4 and 6. In one example, first programmable gain amplifier stage 214a is a programmable gain differential amplifier stage to further amplify a differential sensor signal from high-pass filter stage 212. First programmable gain amplifier stage 214a may include a first chopper programmable gain amplifier stage. In response to the first bypass switch 216a being open, the first programmable gain amplifier stage 214a further amplifies the sensor signal from high-pass filter stage 212. In response to the first bypass switch 216a being closed, the first programmable gain amplifier stage 214a is bypassed and the sensor signal on signal path 222 is passed to signal path 224.

The second programmable gain amplifier stage 214b may further amplify the sensor signal from first programmable gain amplifier stage 214a. Second programmable gain amplifier stage 214b may include programmable gain amplifier stage 400 or 600 to be described below with reference to FIGS. 4 and 6. In one example, second programmable gain amplifier stage 214b is a programmable gain differential amplifier stage to further amplify a differential sensor signal from first programmable gain amplifier stage 214a. Second programmable gain amplifier stage 214b may include a second chopper programmable gain amplifier stage. In response to the second bypass switch 216b being open, the second programmable gain amplifier stage 214b further amplifies the sensor signal on signal path 224 (i.e., the sensor signal from first programmable gain amplifier stage 214a if first bypass switch 216a is open or from signal path 222 if first bypass switch 216a is closed). In response to the second bypass switch 216b being closed, the second programmable gain amplifier stage 214b is bypassed and the sensor signal on signal path 224 is passed to signal path 226.

Analog to digital converter 218 converts the analog sensor signal on signal path 226 to generate a digital value on signal path 228 corresponding to the analog sensor signal. In one example, analog to digital converter 218 is a differential analog to digital converter. The digital value on signal path 228 may be used to control a stimulation engine or for other suitable purposes.

Controller 220 may control high-pass filter stage 212, first programmable gain amplifier stage 214a, first bypass switch 216a, second programmable gain amplifier stage 214b, and second bypass switch 216b. Controller 220 may include a central processing unit (CPU), microprocessor, microcontroller, application-specific integrated circuit (ASIC), and/or other suitable logic circuitry for controlling the operation of device 200. Controller 220 may include a memory storing machine-readable instructions (e.g., firmware) executed by the controller for controlling the operation of device 200.

In some examples, the controller 220 in FIG. 2B may comprise at least a portion of the control portion 1300 described later in association with FIG. 10A, or control portion 1300 in FIG. 10A may comprise one example implementation of controller 220 in FIG. 2B.

Figure 3:
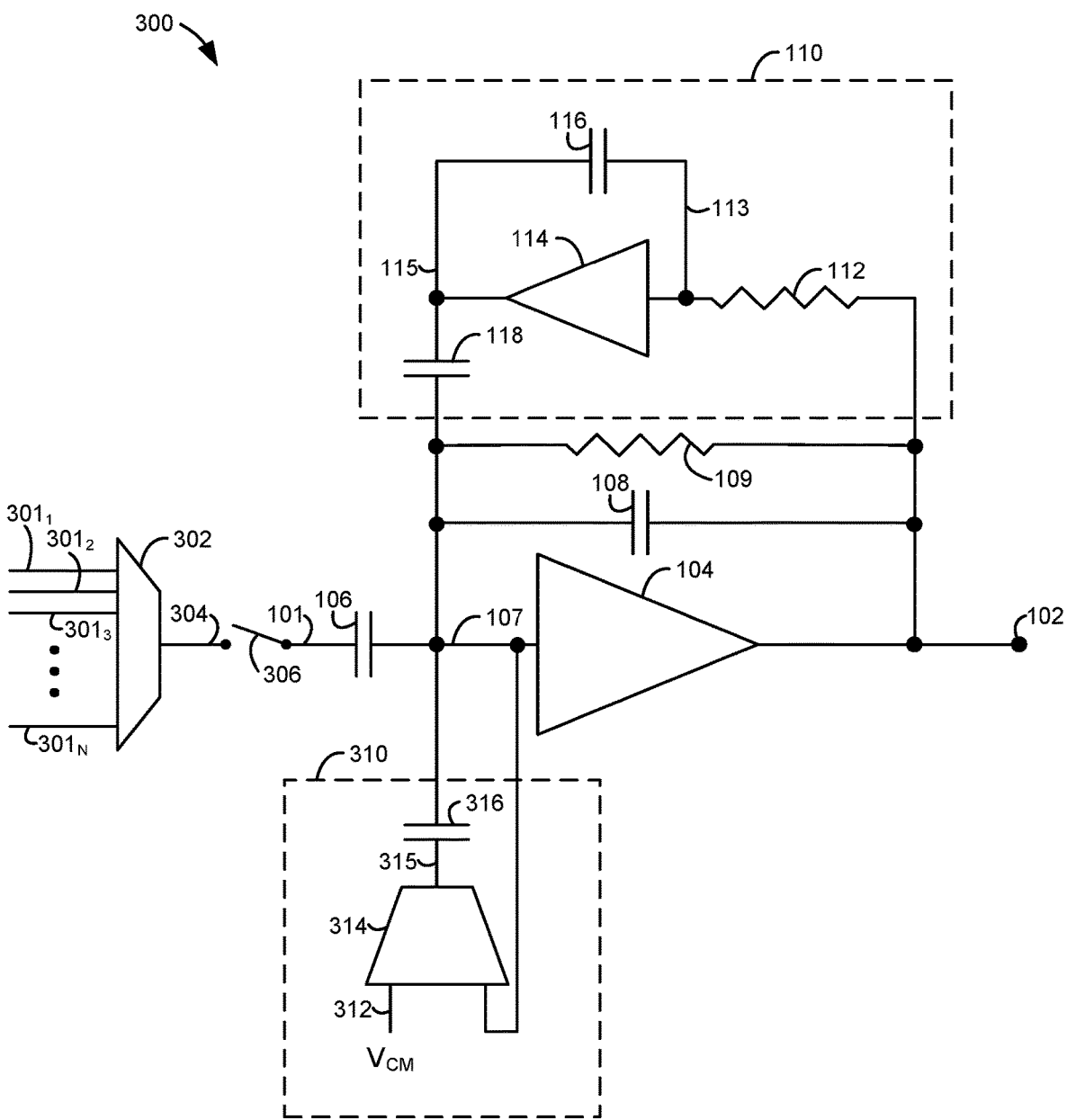
FIG. 3 is a schematic diagram illustrating another example of a device including a high-pass filter stage.

FIG. 3 is a schematic diagram illustrating another example of a device including a high-pass filter stage 300. In some examples, the high-pass filter stage 300 may be part of sensing element 14 of FIGS. 1A-1D. High-pass filter stage 300 is similar to high-pass filter stage 100 previously described and illustrated with reference to FIG. 2A, except that high-pass filter stage 300 also includes a multiplexer 302, a blanking switch 306, and an input common-mode feedback regulator 310. Input common-mode feedback regulator 310 includes a reference voltage ($V_{CM}$) node 312, an input common-mode feedback regulation operational transconductance amplifier (OTA) 314, and a capacitor 316.

Multiplexer 302 is electrically coupled between a plurality of electrode nodes $301_1$ to $301_N$ and a sensor signal input node 304, where "N" is any suitable number of electrodes (e.g., 8). Blanking switch 306 is electrically coupled between the sensor signal input node 304 and the sensor signal input node 101. The reference voltage node 312 is electrically coupled to a first input of OTA 314. The input node 107 of operational amplifier 104 is electrically coupled to a second input of OTA 314. The output of OTA 314 is electrically coupled to one side of capacitor 316 through a signal path 315. The other side of capacitor 316 is electrically coupled to input node 107 of operational amplifier 104.

Multiplexer 302 selectively couples one of the plurality of electrode nodes $301_1$ to $301_N$ to the sensor signal input node 304 in response to an electrode selection signal (e.g., from controller 220 of FIG. 2B). Each electrode node $301_1$ to $301_N$ may be electrically coupled to a sensor, such as a sensor 202 of FIG. 2B. Blanking switch 306 selectively connects the sensor signal input node 304 to the sensor signal input node 101 in response to a control signal (e.g., from controller 220 of FIG. 2B). With blanking switch 306 closed, a sensor measurement may be obtained. With blanking switch 306 open, a voltage on the selected electrode node $301_1$ to $301_N$ due to a task signal (e.g., stimulation from a stimulation engine) may be masked. The opening and closing of blanking switch 306 may be controlled by the task engine (e.g., stimulation engine), such that sensor (e.g., physiologic sensor) measurements are timed to be obtained between the task events (e.g., stimulation events). By timing the sensor (e.g., physiologic sensor) measurements using blanking switch 306, the saturation of high-pass filter 300 is prevented.

In addition, task signals (e.g., stimulation pulses) delivered at or near the same time as the sensing of biological signals may add measurement error to measurements as the electrode-tissue interface contains capacitive elements, which may temporarily store charge from the task signals leading to residual voltages and currents. The measurement error may be exacerbated when the task signals and sensing circuits share one or more electrodes. The measurement error may be mitigated by using blanking switch 306 as described below.

In some examples, task events (e.g., stimulation events) may be synchronous with the sensing of biological signals. The sensing rate may be faster (by an integer multiple N) than the task rate. In this case, every N measurements may be blanked (using switch 306) or skipped (e.g., not taken) to minimize measurement error due to task events (e.g., stimulation pulses). Alternatively, the task event rate may be faster (by an integer multiple M) than the sensing rate. In this case, every M task events may be skipped (e.g., not delivered) to minimize measurement error due to task events.

In other examples, task events may be asynchronous with the sensing of biological signals. In this case, biological signal measurements due to be obtained at the same time as a task event (e.g., stimulation pulses) may be blanked (using switch 306) or skipped (e.g., not taken) to minimize measurement error. Optionally, a measurement may be blanked or skipped if the measurement is not due to be obtained at the same time as a task event but is due to be obtained within a threshold before the task event. Alternatively, task events due to be delivered at the same time as the sensing of a biological signal may be skipped (e.g., not delivered) to minimize measurement error. Optionally, a task event may be skipped if the task event is not due to be delivered at the same time as the sensing of a biological signal but is due to be delivered within a threshold before the sensing of a biological signal.

Input common-mode feedback regulator 310 senses the input common-mode voltage on input node 107 of operational amplifier 104 and regulates the input common-mode voltage towards the reference voltage $V_{CM}$. In one example, the reference voltage $V_{CM}$ is equal to a supply voltage (e.g., $V_{dd}$) for device 300 divided by two. Since the OTA 314 acts on the common-mode signal, noise and offset of the operational amplifier 104 are suppressed by the common-mode rejection ratio (CMRR) at the input.

Figure 4:
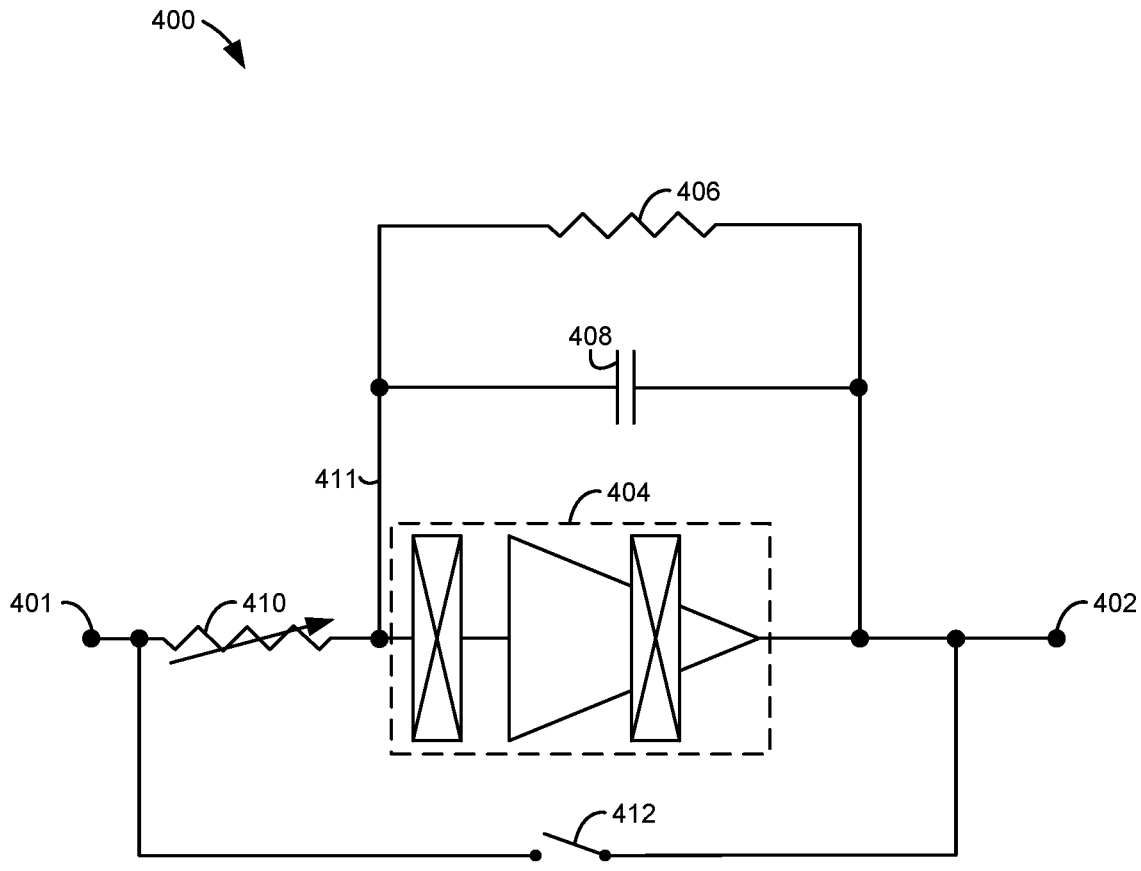
FIG. 4 is a schematic diagram illustrating one example of a programmable gain amplifier stage.

FIG. 4 is a schematic diagram illustrating one example of a programmable gain amplifier stage 400. In one example, programmable gain amplifier stage 400 is a chopper programmable gain amplifier stage. A first programmable gain amplifier stage 400 may be used for the first programmable gain amplifier stage 214a, and a second programmable gain amplifier stage 400 may be used for the second programmable gain amplifier stage 214b of FIG. 2B. Programmable gain amplifier stage 400 includes an input node 401, an output node 402, an operational amplifier 404 (e.g., a chopper amplifier), a feedback resistor 406, a feedback capacitor 408, a programmable input resistor 410, and a bypass switch 412. In one example, programmable input resistor 410 is a pseudo resistor.

Where programmable gain amplifier stage 400 is used for the first programmable gain amplifier stage 214a, the input node 401 may be electrically coupled to the output node 102 of the high-pass filter 100 of FIG. 2A or the high-pass filter 300 of FIG. 3. Where programmable gain amplifier stage 400 is used for second programmable gain amplifier stage 214b, the input node 401 may be electrically coupled to the output node 402 of the first programmable gain amplifier stage.

The input node 401 is electrically coupled to one side of the programmable input resistor 410 and one side of the bypass switch 412. The other side of the programmable input resistor 410 is electrically coupled to the input of the operational amplifier 404, one side of feedback resistor 406, and one side of feedback capacitor 408 through an input node 411 of the operational amplifier 404. The output of operational amplifier 404 is electrically coupled to the other side of the feedback resistor 406, the other side of the feedback capacitor 408, and the other side of the bypass switch 412 through the output node 402.

In one example, where programmable gain amplifier stage 400 is used as first programmable gain amplifier stage 214a of FIG. 2B, bypass switch 412 provides first bypass switch 216a. Likewise, where programmable gain amplifier stage 400 is used as second programmable gain amplifier stage 214b of FIG. 2B, bypass switch 412 provides second bypass switch 216b. In response to bypass switch 412 being closed, the programmable gain amplifier stage 400 is bypassed and the sensor signal on the input node 401 is passed to the output node 402. In response to bypass switch 412 being open, the programmable gain amplifier stage 400 amplifies the sensor signal on the input node 401 to provide an amplified sensor signal on the output node 402.

The gain of programmable gain amplifier stage 400 is adjusted by programming programmable input resistor 410. In one example, programmable gain amplifier stage 400 may be programmed to have a gain of about 10 or about 20. The bandwidth of programmable gain amplifier stage 400 is defined by the feedback resistor 406 and the feedback capacitor 408. In one example, the feedback resistor 406 and the feedback capacitor 408 are selected such that programmable gain amplifier stage 400 has a bandwidth of about 500 Hz.

Figure 5:
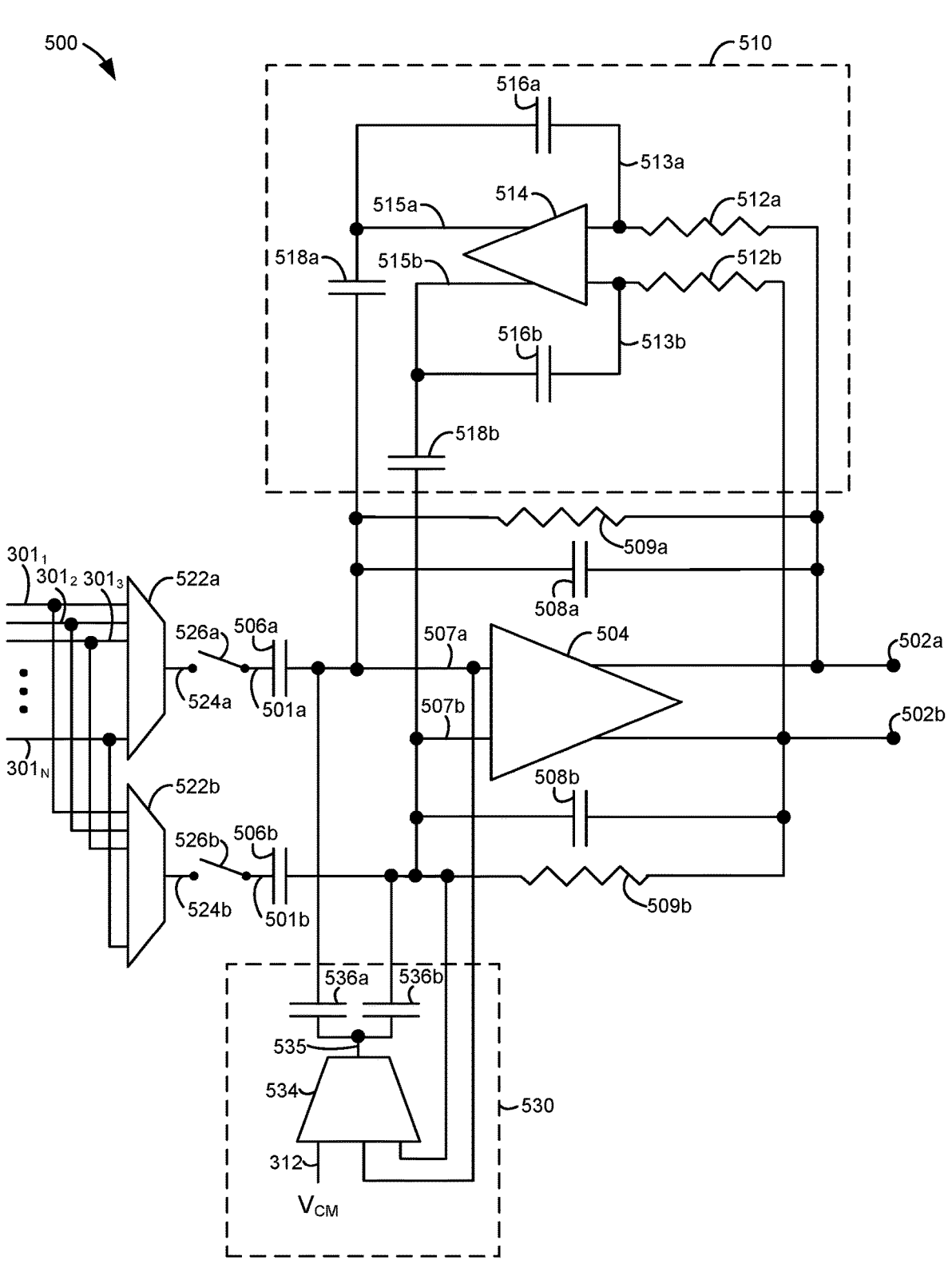
FIG. 5 is a schematic diagram illustrating another example of a high-pass filter stage.

FIG. 5 is a schematic diagram illustrating another example of a high-pass filter stage 500. High-pass filter stage 500 is a fully differential high-pass filter stage. In one example, high-pass filter stage 500 is used for high-pass filter stage 212 of FIG. 2B. High-pass filter stage 500 includes the plurality of electrode nodes $301_1$ to $301_N$ previously described and illustrated with reference to FIG. 3. In addition, high-pass filter stage 500 includes a first output node 502a, a second output node 502b, a fully differential operational amplifier 504, a first input capacitor 506a, a second input capacitor 506b, a first feedback capacitor 508a, a second feedback capacitor 508b, a first resistor 509a, a second resistor 509b, a first multiplexer 522a, a second multiplexer 522b, a first blanking switch 526a, and a second blanking switch 526b. High-pass filter stage 500 also includes a feedback integrator 510 and an input common-mode feedback regulator 530.

Feedback integrator 510 includes a first input resistor 512a, a second input resistor 512b, a feedback amplifier 514, a first feedback capacitor 516a, a second feedback capacitor 516b, a first output capacitor 518a, and a second output capacitor 518b. In one example, the first input resistor 512a is a pseudo resistor, and the second input resistor 512b is a pseudo resistor. Input common-mode feedback regulator 530 includes a reference voltage ($V_{CM}$) node 312, an input common-mode feedback regulation operational transconductance amplifier (OTA) 534, a first capacitor 536a, and a second capacitor 536b.

Each electrode node $301_1$ to $301_N$ is electrically coupled to an input of the first multiplexer 522a and an input of the second multiplexer 522b. The output of first multiplexer 522a is electrically coupled to one side of the first blanking switch 526a through a positive sensor signal input node 524a. The output of second multiplexer 522b is electrically coupled to one side of the second blanking switch 526b through a negative sensor signal input node 524b. The other side of the first blanking switch 526a is electrically coupled to one side of first input capacitor 506a through a signal path 501a. The other side of the second blanking switch 526b is electrically coupled to one side of second input capacitor 506b through a signal path 501b. The other side of the first input capacitor 506a is electrically coupled to a first input of the fully differential operational amplifier 504, one side of the first feedback capacitor 508a, one side of the first resistor 509a, one side of the first output capacitor 518a, and one side of the first capacitor 536a through a first input node 507a of the fully differential operational amplifier 504. The other side of the second input capacitor 506b is electrically coupled to a second input of the fully differential operational amplifier 504, one side of the second feedback capacitor 508b, one side of the second resistor 509b, one side of the second output capacitor 518b, and one side of the second capacitor 536b through a second input node 507b of the fully differential operational amplifier 504.

A first output of the fully differential operational amplifier 504 is electrically coupled to the other side of the first feedback capacitor 508a, the other side of the first resistor 509a, and one side of the first input resistor 512a through the first output node 502a. A second output of the fully differential operational amplifier 504 is electrically coupled to the other side of the second feedback capacitor 508b, the other side of the second resistor 509b, and one side of the second input resistor 512*b* through the second output node 502*b*. The other side of the first input resistor 512*a* is electrically coupled to a first input of feedback amplifier 514 and one side of first feedback capacitor 516*a* through a signal path 513*a*. The other side of the second input resistor 512*b* is electrically coupled to a second input of feedback amplifier 514 and one side of second feedback capacitor 516*b* through a signal path 513*b*. A first output of feedback amplifier 514 is electrically coupled to the other side of first feedback capacitor 516*a* and the other side of first output capacitor 518*a* through a signal path 515*a*. A second output of feedback amplifier 514 is electrically coupled to the other side of second feedback capacitor 516*b* and the other side of second output capacitor 518*b* through a signal path 515*b*.

The reference voltage node 312 is electrically coupled to a first input of OTA 534. The first input node 507*a* of fully differential operational amplifier 504 is electrically coupled to a second input of OTA 534. The second input node 507*b* of fully differential operational amplifier 504 is electrically coupled to a third input of OTA 534. The output of OTA 534 is electrically coupled to the other side of first capacitor 536*a* and the other side of second capacitor 536*b* through a signal path 535.

In one example, the capacitance of first input capacitor 506*a* equals the capacitance of second input capacitor 506*b*. The capacitance of first feedback capacitor 508*a* equals the capacitance of second feedback capacitor 508*b*. The resistance of first resistor 509*a* equals the resistance of second resistor 509*b*. The resistance of first input resistor 512*a* equals the resistance of second input resistor 512*b*. The capacitance of first feedback capacitor 516*a* equals the capacitance of second feedback capacitor 516*b*. The capacitance of first output capacitor 518*a* equals the capacitance of second output capacitor 518*b*. The capacitance of first capacitor 536*a* equals the capacitance of second capacitor 536*b*.

First multiplexer 522*a* selectively couples one of the plurality of electrode nodes 301$_1$ to 301$_N$ to the positive sensor signal input node 524*a* in response to a first electrode selection signal (e.g., from controller 220 of FIG. 2B). Second multiplexer 522*b* selectively couples another one of the plurality of electrode nodes 301$_1$ to 301$_N$ to the negative sensor signal input node 524*b* in response to a second electrode selection signal (e.g., from controller 220 of FIG. 2B).

The feedback integrator 510 sets a high-pass pole frequency of the high-pass filter stage 500. A first output voltage of the feedback amplifier 514 is connected via first output capacitor 518*a* to the first input node 507*a* of the fully differential operational amplifier 504 to convert this first voltage to a first current. A second output voltage of the feedback amplifier 514 is connected via second output capacitor 518*b* to the second input node 507*b* of the fully differential operational amplifier 504 to convert this second voltage to a second current. On first input node 507*a*, the first current from feedback integrator 510 is summed with a first input current from first input capacitor 506*a*. On second input node 507*b*, the second current from feedback integrator 510 is summed with a second input current from second input capacitor 506*b*. In one example, the capacitance of the first output capacitor 518*a* is selected to be one-tenth the capacitance of the first input capacitor 506*a*, and the capacitance of the second output capacitor 518*b* is selected to be one-tenth the capacitance of the second input capacitor 506*b*. In this example, therefore, a 100 mV differential swing at the sensor input nodes 501*a* and 501*b* will be cancelled by integrating 1 V on first output capacitor 518*a* and second output capacitor 518*b*. The first resistor 509*a* in parallel with the first feedback capacitor 508*a* and the second resistor 509*b* in parallel with the second feedback capacitor 508*b* prevent saturation of the feedback amplifier 514 by providing a DC path for first input node 507*a* and second input node 507*b*, respectively.

First blanking switch 526*a* selectively connects the positive sensor signal input node 524*a* to the first sensor signal input node 501*a* in response to a control signal (e.g., from controller 220 of FIG. 2B). Second blanking switch 526*b* selectively connects the negative sensor signal input node 524*b* to the second sensor signal input node 501*b* in response to a control signal (e.g., from controller 220 of FIG. 2B). With first blanking switch 526*a* and second blanking switch 526*b* closed, a sensor measurement may be obtained. With first blanking switch 526*a* and second blanking switch 526*b* open, voltages on the selected electrodes due to a task signal (e.g., stimulation, other) from a task engine (e.g., stimulation engine, other) may be masked. The opening and closing of first blanking switch 526*a* and second blanking switch 526*b* may be controlled by the task engine (e.g., stimulation engine) such that sensor (e.g., physiologic sensor) measurements are timed to be obtained between task events (e.g., stimulation events). By timing the sensor measurements using first blanking switch 526*a* and second blanking switch 526*b*, the saturation of high-pass filter 500 is prevented, thereby preserving the ability to maintain high sensitivity in sensing physiological signals and/or other types of signals having very small amplitudes or other fine characteristics.

Input common-mode feedback regulator 530 senses the input common-mode voltage on first input node 507*a* and second input node 507*b* of fully differential operational amplifier 504 and regulates the input common-mode voltage towards the reference voltage $V_{CM}$. Since the OTA 534 acts on the common-mode signal, noise and offset of the fully differential operational amplifier 504 are suppressed by the common-mode rejection ratio (CMRR) at the input.

Figure 6:
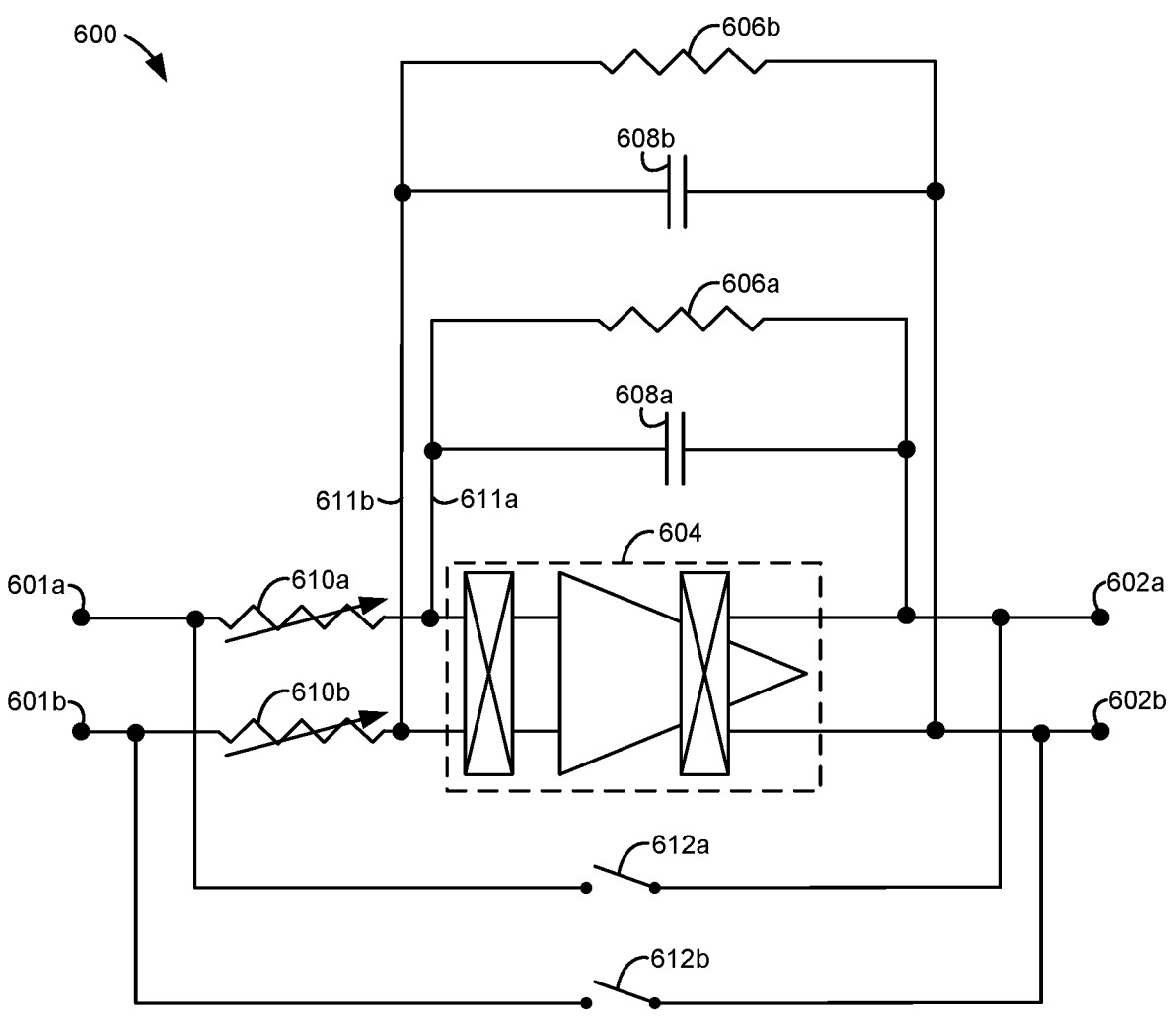
FIG. 6 is a schematic diagram illustrating another example of a programmable gain amplifier stage.

FIG. 6 is a schematic diagram illustrating another example of a programmable gain amplifier stage 600. Programmable gain amplifier stage 600 is a programmable gain differential amplifier stage. In one example, programmable gain differential amplifier stage 600 is a chopper programmable gain differential amplifier stage. A first programmable gain differential amplifier stage 600 may be used for the first programmable gain amplifier stage 214*a*, and a second programmable differential gain amplifier stage 600 may be used for the second programmable gain amplifier stage 214*b* of FIG. 2B.

Programmable gain differential amplifier stage 600 includes a first input node 601*a*, a second input node 601*b*, a first output node 602*a*, a second output node 602*b*, a fully differential operational amplifier 604 (e.g., a fully differential chopper amplifier), a first feedback resistor 606*a*, a second feedback resistor 606*b*, a first feedback capacitor 608*a*, a second feedback capacitor 608*b*, a first programmable input resistor 610*a*, a second programmable input resistor 610*b*, a first bypass switch 612*a*, and a second bypass switch 612*b*. In one example, first programmable input resistor 610*a* is a first programmable pseudo input resistor, and the second programmable input resistor 610*b* is a second programmable pseudo input resistor.

Where programmable gain differential amplifier stage 600 is used for first programmable gain amplifier stage 214*a*, the first input node 601*a* may be electrically coupled to the first output node 502*a*, and the second input node 601*b* may be electrically coupled to the second output node 502*b* of the high-pass filter 500 of FIG. 5. Where programmable gain differential amplifier stage 600 is used for second programmable gain amplifier stage 214b, the first input node 601a may be electrically coupled to the first output node 602a of the first programmable gain amplifier stage, and the second input node 601b may be electrically coupled to the second output node 602b of the first programmable gain amplifier stage. Where programmable gain differential amplifier stage 600 is used for second programmable gain amplifier stage 214b, the first output node 602a and the second output node 602b are electrically coupled to inputs of a differential analog to digital converter (e.g., analog to digital converter 218 of FIG. 2B).

The first input node 601a is electrically coupled to one side of the first programmable input resistor 610a and one side of the first bypass switch 612a. The second input node 601b is electrically coupled to one side of the second programmable input resistor 610b and one side of the second bypass switch 612b. The other side of the first programmable input resistor 610a is electrically coupled to a first input of the fully differential operational amplifier 604, one side of first feedback resistor 606a, and one side of first feedback capacitor 608a through a first input node 611a of the fully differential operational amplifier 604. The other side of the second programmable input resistor 610b is electrically coupled to a second input of the fully differential operational amplifier 604, one side of second feedback resistor 606b, and one side of second feedback capacitor 608b through a second input node 611b of the fully differential operational amplifier 604. A first output of fully differential operational amplifier 604 is electrically coupled to the other side of the first feedback resistor 606a, the other side of the first feedback capacitor 608a, and the other side of the first bypass switch 612a through the first output node 602a. A second output of fully differential operational amplifier 604 is electrically coupled to the other side of the second feedback resistor 606b, the other side of the second feedback capacitor 608b, and the other side of the second bypass switch 612b through the second output node 602b.

In one example, the resistance of first feedback resistor 606a is equal to the resistance of second feedback resistor 606b. The capacitance of first feedback capacitor 608a is equal to the capacitance of second feedback capacitor 608b. The programmed resistance of first programmable input resistor 610a is equal to the programmed resistance of second programmable input resistor 610b.

In one example, where programmable gain differential amplifier stage 600 is used as first programmable gain amplifier stage 214a of FIG. 2B, first bypass switch 612a and second bypass switch 612b provide first bypass switch 216a. Likewise, where programmable gain differential amplifier stage 600 is used as second programmable gain amplifier stage 214b of FIG. 2B, first bypass switch 612a and second bypass switch 612b provide second bypass switch 216b. In response to the first bypass switch 612a and the second bypass switch 612b being closed, the programmable gain differential amplifier stage 600 is bypassed and the first input node 601a is connected to the first output node 602a and the second input node 601b is connected to the second output node 602b. In response to first bypass switch 612a and the second bypass switch 612b being open, the programmable gain differential amplifier stage 600 amplifies the differential signal on the first input node 601a and the second input node 601b to provide an amplified differential signal on the first output node 602a and the second output node 602b.

The gain of programmable gain differential amplifier stage 600 is adjusted by programming first programmable input resistor 610a and second programmable input resistor 610b. In one example, programmable gain differential amplifier stage 600 may be programmed to have a gain of about 10 or about 20. The bandwidth of programmable gain differential amplifier stage 600 is defined by the first feedback resistor 606a, the first feedback capacitor 608a, the second feedback resistor 606b, and the second feedback capacitor 608b. In one example, the first feedback resistor 606a, the first feedback capacitor 608a, the second feedback resistor 606b, and the second feedback capacitor 608b are selected such that programmable gain differential amplifier stage 600 has a bandwidth of about 500 Hz.

FIGS. 7A-7F are a series of flow diagrams schematically representing an example method 700. In some examples, method 700 may be implemented by the devices described and illustrated with reference to FIGS. 2A-6. As illustrated in FIG. 7A at 710, method 700 includes receiving a sensor signal at a sensor signal input node (e.g., node 101 of FIG. 2A, node 304 of FIG. 3, or nodes 524a, 524b of FIG. 5). At 712, method 700 includes filtering the received sensor signal via a high-pass filter stage (e.g., stage 100 of FIG. 2A, stage 212 of FIG. 2B, stage 300 of FIG. 3, or stage 500 of FIG. 5). At 714, filtering the received sensor signal via the high-pass filter stage may include amplifying the received sensor signal via an operational amplifier (e.g., amplifier 104 of FIGS. 2A and 3 or amplifier 504 of FIG. 5) comprising an input node (e.g., node 107 of FIGS. 2A and 3 or nodes 507a, 507b of FIG. 5) coupled to the sensor signal input node. At 716, filtering the received sensor signal via the high-pass filter stage may include integrating feedback of the operational amplifier between an output node (e.g., node 102 of FIGS. 2A and 3 or nodes 502a, 502b of FIG. 5) of the operational amplifier and the input node of the operational amplifier to set a high-pass pole frequency of the high-pass filter stage (e.g., via feedback integrator 110 of FIGS. 2A and 3 or feedback integrator 510 of FIG. 5). In some examples, filtering the received sensor signal via the high-pass filter stage may further include rejecting input common-mode signals at the input node of the operational amplifier (e.g., via input common-mode feedback regulator 310 of FIG. 3 or input common-mode feedback regulator 530 of FIG. 5).

As illustrated in FIG. 7B at 718, method 700 may further include selectively blanking a task signal to prevent the task signal from being input to the operational amplifier (e.g., via switch 306 of FIG. 3 or switches 526a, 526b of FIG. 5). As illustrated in FIG. 7C at 720, method 700 may further include selectively coupling the sensor signal input node to one of a plurality of electrode nodes in response to an electrode selection signal (e.g., via multiplexer 302 of FIG. 3 or multiplexers 522a, 522b of FIG. 5). As illustrated in FIG. 7D at 722, method 700 may further include amplifying, via a first programmable gain amplifier stage (e.g., stage 214 of FIG. 2B), the filtered sensor signal on the output node of the operational amplifier. As illustrated in FIG. 7E at 724, method 700 may further include amplifying, via a second programmable gain amplifier stage (e.g., stage 214b of FIG. 2B), the filtered and amplified sensor signal on an output node of the first programmable gain amplifier stage. As illustrated in FIG. 7F at 726, method 700 may further include converting the filtered and amplified sensor signal on an output node of the second programmable gain amplifier stage to a digital value (e.g., via ADC 218 of FIG. 2B).

It will be understood that the examples in FIGS. 2A-7F may comprise example implementations of, or comprise at least some of substantially the same features and attributes of, the example arrangements (e.g., devices and/or methods) described in association with at least FIGS. 1A-1D and FIGS. 8A-11C.

Figures 8A, 8B, 8C:
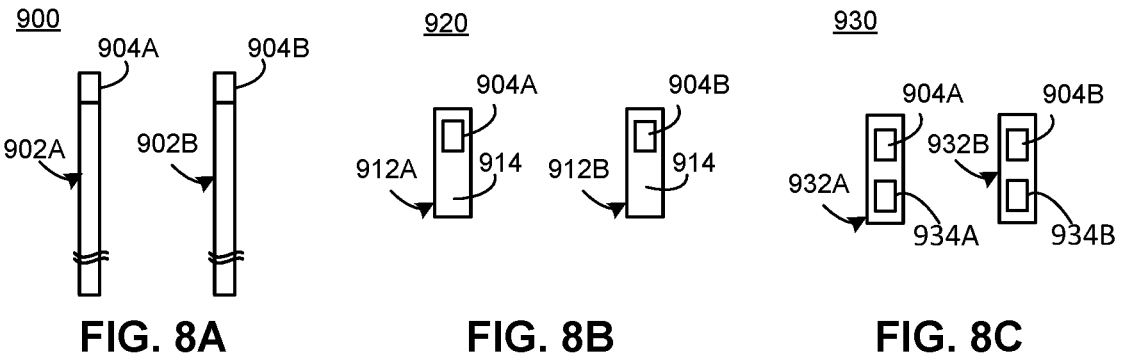
FIGS. 8A-8E are a series of diagrams schematically representing example electrode arrangements for sensing and/or tasks.

FIG. 8A is a diagram schematically representing an example arrangement 900 including a pair of spaced apart leads 902A, 902B, each of which includes a respective electrode 904A, 904B. In some examples, when placed in proximity to a target (e.g., the targets in FIGS. 1A-1D), the electrodes 904A, 904B may be used to sense information regarding the target. In some such examples, the sensed information may comprise an impedance associated with the target.

It will be further understood that either or both electrodes 904A, 904B may comprise an array of electrodes.

In some examples, the electrodes 904A, 904B may be used solely for sensing. However, in some examples, the electrodes 904A, 904B may be used as task elements (e.g., 25) to apply a task signal (e.g., 26 in FIGS. 1A-1D) and/or used for sensing (e.g., 12 in FIGS. 1A-1D). In some such examples, the electrodes 904A, 904B may be used for sensing at times when the same electrodes 904A, 904B are not being used for applying a task signal, or vice versa. In some examples, lead 902A may comprise more than one electrode 904A and lead 902B may comprise more than one electrode 904B such that each lead 902A, 902B has at least some electrodes used solely for sensing and at least some electrodes used solely for stimulation.

In some examples, in which the leads 902A, 902B are deployed to sense physiologic phenomenon, the leads 902A, 902B and their respective electrodes 904A, 904B may be deployed in any one or more of the various portions of a patient's body 1000 as further described later in association with at least FIG. 8F.

FIG. 8B is a diagram schematically representing an example arrangement 920 including a pair of spaced apart microstimulators 912A, 912B, each of which includes a respective electrode 904A, 904B on a body 914. In some examples, the electrodes 904A, 904B may comprise at least some of substantially the same features and attributes as described in association with FIG. 8A, except arranged on microstimulator 912A, 912B instead of on leads 902A, 902B. Each microstimulator 912A, 912B may comprise power elements, circuitry, etc. for applying a stimulation signal. In some examples, the microstimulator may comprise a battery, which may be rechargeable, or may comprise another type of power source. In some examples, each microstimulator may comprise a micro task signal generator in which a signal generated and applied relates to a task, which may be other than stimulation.

FIG. 8C is a diagram schematically representing an example arrangement 930 including a pair of spaced apart microstimulators 932A, 932B, which may comprise at least some of substantially the same features and attributes as described in association with FIG. 8B, except with multiple electrodes 904A, 934A on microstimulator 932A and multiple electrodes 904B, 934B on microstimulator 932B.

With respect to FIGS. 8B-8C, in some examples, in which the microstimulators 912A, 912B (or 932A, 932B) are deployed to sense physiologic phenomenon, the microstimulators 912A, 912B (or 932A, 932B) and their respective electrodes may be deployed in any one or more of the various portions of a patient's body 1000 as further described later in association with at least FIG. 8F.

Figures 8D, 8E:
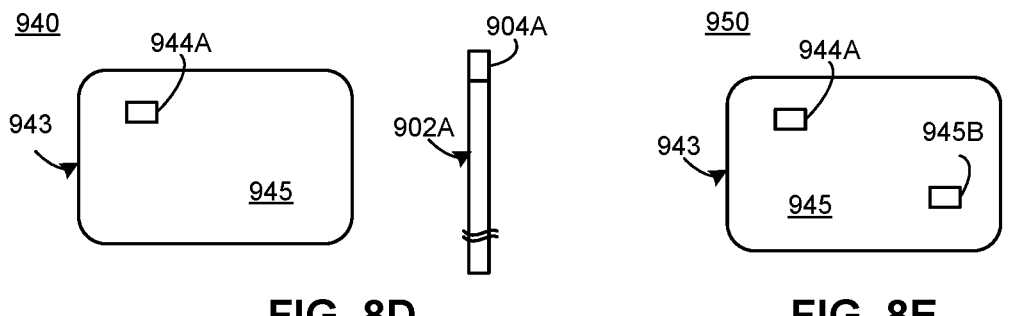

FIG. 8D is a diagram schematically representing an example arrangement 940 including a pair of spaced apart electrodes 904A, 944A. In some examples, the electrodes 904A, 944A may comprise at least some of substantially the same features and attributes as the electrodes 904A, 904B described in association with FIG. 8A, except with electrode 944A arranged on a body 945 of a task signal generator 943 (instead of on a lead 902B) to be spaced apart from electrode 904A on lead 902A. The task signal generator 943 may take a wide variety of shapes and forms, depending on the type of task signal, location or environment in which it is applied, etc. In some examples, such as when the task signal generator 943 may comprise an implantable pulse generator (IPG), it may take a form suitable for implantation within a body, and may be used to apply a stimulation signal or other impact signal to a target within a patient's body.

Via this example arrangement, electrode 904A on lead 902A may be placed in proximity to a target to be sensed and/or a target to which a task signal is to be applied. Meanwhile, the task signal generator 943 may be placed at a location such that the electrode 944A is spaced apart from the electrode 904A on lead 902A with some portion of target therebetween to enable sensing a parameter, such as an impedance of the target between the respective electrodes 904A, 944A. In some such examples, the lead 902A extends from, and is electrically connected to, the task signal generator 943, which may support use of the electrode 904A as part of a sensing element (e.g., 14 in FIG. 1A) and/or as part of a task element 25 (e.g., FIG. 1B) with electrode 944A working together with spaced apart electrode 904A.

FIG. 8E is a diagram schematically representing an example arrangement 950 including a task signal generator 943 including a pair of spaced apart electrodes 944A, 945B. In some examples, electrodes 944A, 945B may comprise at least some of substantially the same features and attributes as described in association with FIG. 8A, except with both respective electrodes 944A, 945B arranged on a body 945 of the task signal generator 943. In some such examples, both electrodes 944A, 945B may function together as a sensing element and may or may not serve a function (e.g., sensing, task, etc.) in relation to another electrode spaced apart from the task signal generator 943.

As noted elsewhere, in some examples a task signal may comprise a stimulation signal, such as for stimulation of a nerve, muscle etc.

Figure 8F:
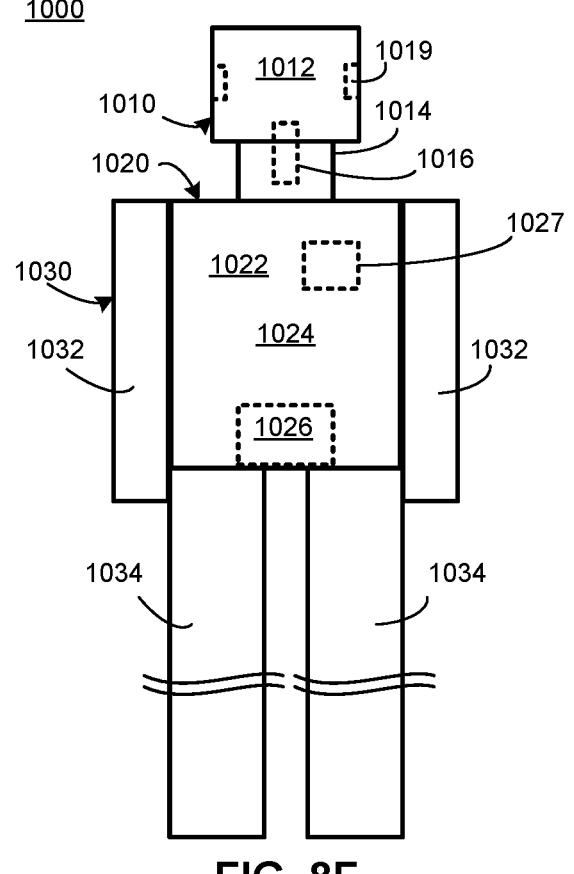
FIG. 8F is a block diagram schematically representing an example patient body, including example target zones for sensing and/to which a task signal may be applied.

FIG. 8F is block diagram schematically representing a patient's body 1000, including example target portions 1010-1034 at which at least some of the example sensing elements and/or example task elements may be employed to implement at least some examples of the present disclosure.

As shown in FIG. 8F, patient's body 1000 comprises a head-and-neck portion 1010, including head 1012 and neck 1014. Head 1012 comprises cranial tissue, nerves, etc., which may include auditory portions 1019 (e.g., hearing organs, nerves) and upper airway 1016 (e.g., nerves, muscles, tissues), etc. The tissues, nerves, etc. within the head-and-neck portion 1010 may be sensed (e.g., EEG) and/or may receive a task signal, such as a magnetic stimulation signal or electrical stimulation signal to treat upper airway patency.

As further shown in FIG. 8F, the patient's body 1000 comprises a torso 1020, which comprises various organs, muscles, nerves, other tissues, such as but not limited to those in pectoral region 1022 (e.g., cardiac 1027), abdomen 1024, and/or pelvic region 1026 (e.g., urinary/bladder, anal, reproductive, etc.).

As further shown in FIG. 8F, the patient's body 1000 comprises limbs 1030, such as arms 1032 and legs 1034.

It will be understood that the various sensing elements 14 and/or task elements 25 (FIGS. 1A-1D) may be deployed within the various regions of the patient's body 1000, according to at least some of the example electrode arrangements in FIGS. 8A-8E in order to sense and/or otherwise diagnose, monitor, treat various physiologic conditions such as, but not limited to those examples described below in association with at least engagement engine 1200 in FIG. 9.

FIG. 9 is a block diagram schematically representing an example engagement engine 1200. In some examples, the engagement engine 1200 may form part of a control portion 1300 (FIG. 10A), such as but not limited to comprising at least part of the instructions 1311. In some examples, the engagement engine 1200 may be used to implement at least some of the various example devices and/or example methods of the present disclosure as previously described in association with FIGS. 1A-8F and/or in later described examples devices and/or methods. In some examples, the engagement engine 1200 and/or control portion 1300 (FIG. 10A) may form part of, and/or be in communication with, the example arrangements, sensing elements, tasking elements, task signal generators, leads, microstimulators, pulse generators, etc. such as a portion of the devices and methods described in association with at least FIGS. 1A-8F and/or the later described examples. It will be understood that various sub-engines, functions, parameters, etc. of engagement engine 1200 may be operated interdependently and/or in coordination with each other, in at least some examples.

As shown in FIG. 9, the engagement engine 1200 may comprise a sense sub-engine 1202 to track and/or control sensing of, or at, a target, such as described in association with FIGS. 1A-1F, 8A-8F, and/or 9. Engagement engine 1200 also may comprise a task sub-engine 1204 to track and/or control implementation of a task via a task signal, such as described in association with FIGS. 1A-1F, 8A-8F, and/or 9.

In some examples, engagement engine 1200 may comprise a physiologic target sub-engine 1210, which may track and/or control sensing of a physiologic target and/or application of a task signal relative to a physiologic target. In some such examples, the sub-engine 1210 may sense and/or apply a task signal relative to tissue (parameter 1211), which may comprise a nerve(s) 1212, muscle(s) 1214, connective tissue 1216, organ 1218, and/or other tissues.

In some examples, the physiologic target sub-engine 1210 may track and/or control sensing and/or tasking in relation to a physiologic function (parameter 1222), a physiologic behavior (parameter 1224), a physiologic system (parameter 1226), and/or a physiologic type (parameter 1228). Various examples of such functions, behaviors, systems, types are described throughout the various examples associated with at least FIG. 9.

As further shown in FIG. 9, in some examples the task sub-engine 1204 may comprise, or be implemented, as a task type sub-engine 1240, which may comprise an impact sub-engine 1242 when a task signal is implemented as an impact signal. In some such examples, an impact signal may comprise a stimulation signal 1243 and/or other signal 1245. In some examples, the stimulation signal 1243 may comprise an electrical stimulation signal, such as for stimulating a nerve, muscle, etc. However, in some examples, the stimulation signal 1243 may comprise a magnetic stimulation signal such as but not limited to a transcranial magnetic stimulation (TOMS) signal for stimulating cranial tissue (nervous system 1262) related to improving depression symptoms.

In some examples, the physiologic system (parameter 1226) of the physiologic target sub-engine 1210 may be implemented per a system sub-engine 1260 to track and/or control sensing and/or a task in relation to a cardiac system

1261, a nervous system 1262, a respiratory system 1263, an upper airway system 1264, a pelvic system 1265, and/or other physiologic system 1269.

In some examples, the tracking and/or the controlling of sensing and/or a task for the nervous system 1262 may comprise such sensing and/or task related to care (e.g., diagnosing, monitoring, treatment, etc.) for nervous system conditions. In some examples, the nervous system may comprise nerves and associated tissues throughout the entire patient's body or a portion of the patient's body such as, but not limited to the spinal cord, cranial tissues, etc. In some examples, sensing neurological signals 1262 may comprise sensing a neural activity and/or action of a nerve. In some examples, sensing may comprise sensing local field potentials, as may be applicable to sensing brain signals or other neurological phenomenon. In some such examples, such as mentioned regarding the stimulation task 1243, such sensing and/or tracking may relate to treating depression and/or other psycho-emotional conditions. In addition, in some examples such as mentioned regarding the below-described task types 1270, such sensing and/or tasking may relate to EEG signals.

In some examples, the tracking and/or the controlling of sensing and/or a task for the respiratory system 1263 and/or upper airway system 1264 may comprise such sensing and/or tasking related to care (e.g., diagnose, monitor, treat, etc.) for sleep disordered breathing such as, but not limited to, obstructive sleep apnea, central sleep apnea, or multiple-type apnea. In some such examples, tasking may comprise applying stimulation to an upper airway patency-related nerve such as, but not limited to, a hypoglossal nerve, ansa cervicalis-related nerve and/or other nerves or muscles which contribute to upper airway patency. In some such examples, stimulation of the hypoglossal nerve and/or other nerves may contribute to at least protrusion of the tongue to enhance upper airway patency. In some examples, stimulation of such nerves (and/or muscles) may enhance upper airway patency by contracting muscles other than the tongue.

In some examples, the tracking and/or the controlling of sensing and/or a task for the pelvic system 1265 may comprise such sensing and/or tasks related to care (e.g., diagnosing, monitoring, treatment, etc.) for pelvic dysfunctions such as, but not limited to, urinary incontinence (e.g., stress, other), fecal incontinence, and so on. In some such examples, the task may comprise electrical stimulation of a pudenal nerve, which controls contraction of an external urinary sphincter, an external anal sphincter, etc.

In some examples, the tracking and/or the controlling of sensing and/or a task for the cardiac system 1261 (and related bodily systems, functions, etc.) may comprise such sensing and/or tasks related to care (e.g., diagnosing, monitoring, treatment, etc.) of cardiac conditions such as, but not limited to, cardiac arrhythmias, atrial fibrillation, ventricular fibrillation, and the like. In some such examples, such sensing and/or tasking may be associated with sensing and/or tasks involving the respiratory system 1263, upper airway system 1264, sleep disordered breathing 1280, and/or tasks 1240.

In some examples, the engagement engine 1200 may sense, and/or apply a task signal relative to, a non-physiologic target per sub-engine 1230, with the non-physiologic target comprising a structural 1232 target and/or other 1234 target. In some such examples, one structural target may comprise structures (e.g., machinery, etc.) built of material susceptible to hidden fatigue failures for which a failure identification signal may be applied to the structure to help identify potential failure sites, failure modes, etc.

In some examples, the task type sub-engine 1240 may comprise tracking and/or control of a communication signal 1246, an investigative signal 1248, or another signal 1247. In some examples, the communication signal 1246 may comprise a telemetry signal or other form of communication signal. In some such examples, the telemetry receive circuitry may be implemented with some or all sections of the various amplifiers (e.g., FIGS. 2A-6) acting as a linear amplifier. The amplifiers in examples of the present disclosure may facilitate telemetry (e.g., inductive or magnetic) from or to an implantable medical device.

In some examples, the investigative signal 1248 may comprise a failure identification signal (e.g., fracture detection), such as described in association with the structural target parameter 1232.

In some examples, the engagement engine 1200 may comprise a sensing type sub-engine 1270 relating to particular types of sensing signals, which may be used to sense one or more of the physiologic or non-physiologic targets described herein. As shown in FIG. 9, in some examples the sensing type engine 1270 may comprise an impedance type 1271 by which sensing of a particular target is performed via sensing an impedance of a target portion such as an impedance between two spaced apart electrodes. At least some example electrode arrangements are described in association with FIGS. 8A-8E. However, it will be understood that in some non-physiologic contexts, other configurations of spaced apart electrodes may be used. As further shown in FIG. 9, in some examples a sensing type may comprise an electroencephalographic (EEG) type 1272 of sensing, an electromyographic (EMG) type 1274 of sensing, an electrocardiographic (ECG) type 1276 of sensing, and/or other type 1277 of sensing involving arrangements of electrodes spaced apart on a physiologic target region of a patient's body (e.g., 1000 in FIG. 8F).

In some examples, the EEG sensing may be used to detect a sleep—wake status 1282 of a patient and/or a neural activity of a nerve. In some examples, the various sensing types may be implemented via at least some features of the examples in FIGS. 1A-1D, FIGS. 8A-8E, and in association with other features of FIG. 9.

In some examples, the engagement engine 1200 may comprise a sleep disordered breathing (SDB) sub-engine 1280 which can track and/or control sensing and/or tasks (e.g., stimulation) related to care (e.g., diagnosing, monitoring, treatment, etc.) for sleep disordered breathing such as, but not limited to, obstructive sleep apnea, central sleep apnea, or multiple-type apnea. In some examples, the sleep disordered breathing sub-engine 1280 may operate in cooperation with, or a complementary manner, with at least the respiratory 1263 and/or upper airway 1264 systems of physiologic systems sub-engine 1260. In some examples, the SDB sub-engine 1280 may track and/or control sensing and/or tasking in relation to SDB-related parameters such as, but not limited to SDB events 1281, sleep-wake detection or status 1282, respiration detection 1283, other SDB parameters 1284, and/or the like.

With regard to all of the various subjects, modalities, parameters, types, etc. of sensing described above in relation to the engagement engine 1200, it will be understood that in some examples, a combination of different subjects, modalities, parameters, types of sensing may be implemented simultaneously wherein a different frequency content of the respectively different subjects, modalities, parameters, types of sensing may allow them to be distinguished from one another. For instance, in some examples, sensing associated with an EEG may be performed simultaneous with sensing associated with an EMG, with such sensing differentiating the two different signals according to their frequency content. In some examples, the general principle of differentiation according to frequency content also may be applicable to simultaneous application of task signals in some examples of the present disclosure.

FIG. 10A is a block diagram schematically representing an example control portion 1300. In some examples, control portion 1300 provides one example implementation of a control portion forming a part of, implementing, and/or generally managing the sensing elements, task elements (e.g., stimulation elements, other), task circuitry (e.g., pulse generators, sensor circuitry, other), sense amplifiers, devices, user interfaces, instructions, information, engines, elements, functions, actions, and/or methods, as described throughout examples of the present disclosure in association with FIGS. 1A-9.

In some examples, control portion 1300 includes a controller 1302 and a memory 1310. In general terms, controller 1302 of control portion 1300 comprises at least one processor 1314 and associated memories. The controller 1302 is electrically couplable to, and in communication with, memory 1310 to generate control signals to direct operation of at least some of sensing elements, task elements (e.g., stimulation elements, other), task circuitry (e.g., pulse generators, sensor circuitry, other), sense amplifiers, devices, user interfaces, instructions, information, engines, elements, functions, actions, and/or methods, as described throughout examples of the present disclosure. In some examples, these generated control signals include, but are not limited to, employing instructions 1311 and/or information stored in memory 1310 to at least direct and manage sensing, applying task signals, and/or related aspects, as described throughout the examples of the present disclosure in association with FIGS. 1A-9. In some such examples, this sensing and/or tasks may comprise treatment of sleep disordered breathing such as obstructive sleep apnea and/or central sleep apnea, sensing physiologic information including but not limited to respiratory information, heart rate, and/or monitoring sleep disordered breathing, etc. In some instances, the controller 1302 or control portion 1300 may sometimes be referred to as being programmed to perform the above-identified actions, functions, etc. In some examples, at least some of the stored instructions 1311 are implemented as, or may be referred to as, an engagement engine. In some examples, at least some of the stored instructions 1311 and/or information may form at least part of, and/or, may be referred to as an engagement engine.

In response to or based upon commands received via a user interface (e.g., user interface 1340 in FIG. 100) and/or via machine readable instructions, controller 1302 generates control signals as described above in accordance with at least some of the examples of the present disclosure. In some examples, controller 1302 is embodied in a general purpose computing device while in some examples, controller 1302 is incorporated into or associated with at least some of the sensing elements, task elements (e.g., stimulation elements, other), task circuitry (e.g., pulse generators, sensor circuitry, other), sense amplifiers, devices, user interfaces, instructions, information, engines, functions, actions, and/or method, etc. as described throughout examples of the present disclosure.

For purposes of this application, in reference to the controller 1302, the term "processor" shall mean a presently developed or future developed processor (or processing resources) that executes machine readable instructions contained in a memory. In some examples, execution of the machine readable instructions, such as those provided via memory 1310 of control portion 1300 cause the processor to perform the above-identified actions, such as operating controller 1302 to implement the apnea treatment as generally described in (or consistent with) at least some examples of the present disclosure. The machine readable instructions may be loaded in a random access memory (RAM) for execution by the processor from their stored location in a read only memory (ROM), a mass storage device, or some other persistent storage (e.g., non-transitory tangible medium or non-volatile tangible medium), as represented by memory 1310. In some examples, the machine readable instructions may comprise a sequence of instructions, a processor-executable machine learning model, or the like. In some examples, memory 1310 comprises a computer readable tangible medium providing non-volatile storage of the machine readable instructions executable by a process of controller 1302. In some examples, the computer readable tangible medium may sometimes be referred to as, and/or comprise at least a portion of, a computer program product. In other examples, hard wired circuitry may be used in place of or in combination with machine readable instructions to implement the functions described. For example, controller 1302 may be embodied as part of at least one application-specific integrated circuit (ASIC), at least one field-programmable gate array (FPGA), and/or the like. In at least some examples, the controller 1302 is not limited to any specific combination of hardware circuitry and machine readable instructions, nor limited to any particular source for the machine readable instructions executed by the controller 1302.

In some examples, control portion 1300 may be entirely implemented within or by a stand-alone device.

In some examples, the control portion 1300 may be partially implemented in one of the example arrangements (or portions thereof) and partially implemented in a computing resource separate from, and independent of, the example arrangements (or portions thereof) but in communication with the example arrangements (or portions thereof). For instance, in some examples, control portion 1300 may be implemented via a server accessible via the cloud and/or other network pathways. In some examples, the control portion 1300 may be distributed or apportioned among multiple devices or resources, such as among a server, an example sensing or tasking arrangement (or portion thereof), and/or a user interface.

In some examples, control portion 1300 includes, and/or is in communication with, a user interface 1340 as shown in FIG. 10C and described below.

FIG. 10B is a diagram schematically illustrating an example arrangement 1320 of at least some example implementations by which the control portion 1300 (FIG. 10A) can be implemented, according to one example of the present disclosure. In some examples, control portion 1300 is entirely implemented within or by a task signal generator 1325 (or sensing monitor), which has at least some of substantially the same features and attributes as a pulse generator (e.g., power/control element, etc.) as previously described throughout the present disclosure. In some examples, control portion 1300 is entirely implemented within or by a remote control 1330 (e.g. a programmer) external to the patient's body, such as a patient control 1332 and/or a clinician control 1334. In some examples, at least some aspects of the control portion 1300 may be implemented within a portal 1336, such as a web portal. In some examples, the control portion 1300 may be partially implemented in the task signal generator 1325 and partially implemented in the remote control 1330 (at least one of patient control 1332 and physician control 1334). In some examples, the remote control 1330 may comprise a smart phone, tablet, smart watch, etc. or other mobile computing device.

FIG. 10C is a block diagram schematically representing user interface 1340, according to one example of the present disclosure. In some examples, user interface 1340 forms part or and/or is accessible via a device external to the patient and by which the therapy system may be at least partially controlled and/or monitored. The external device which hosts user interface 1340 may be a patient remote (e.g., 1332 in FIG. 10B), a physician remote (e.g., 1334 in FIG. 10B) and/or a portal 1336. In some examples, user interface 1340 comprises a user interface or other display that provides for the simultaneous display, activation, and/or operation of at least some of the various sensing elements, task elements (e.g., stimulation elements, other), task circuitry (e.g., pulse generators, sensor circuitry, other), sense amplifiers, devices, instructions, information, engines, functions, and/or methods, as described in association with FIGS. 1A-9. In some examples, at least some portions or aspects of the user interface 1340 are provided via a graphical user interface (GUI), and may comprise a display 1344 and input 1342.

FIG. 11A is a flow diagram schematically representing an example method 1400. In some examples, the method 1400 may be implemented via at least some of substantially the same features and attributes as the sensing elements, task elements (e.g., stimulation elements, other), sensing and/or task circuitry (e.g., pulse generators, sensor circuitry, other), sense amplifiers, devices, user interfaces, instructions, information, engines, elements, functions, actions, and/or methods, as described in association with the examples of FIGS. 1A-10C. In some examples, the method 1400 may be implemented via at least some sensing elements, task elements (e.g., stimulation elements, other), sensor and/or task circuitry (e.g., pulse generators, sensor circuitry, other), sense amplifiers, devices, user interfaces, instructions, information, engines, elements, functions, actions, and/or methods other than those described in association with the examples of FIGS. 1A-10C.

As shown at 1410 in FIG. 11A, in some examples, method 1400 comprises sensing, via a first signal, a first parameter in relation to a first target, and at 1412, method 1400 comprises filtering and amplifying, via a sense amplifier, the sensed first signal.

As further shown at 1422 in FIG. 11B, in some examples, method 1400 of FIG. 11A may further comprise applying, in a same time frame as the sensing, a task signal in relation to a second target, and at 1424, method 1400 may further comprise blocking (blanking) reception of the task signal at, and via, the sense amplifier during the application of the task signal.

As further shown at 1430 in FIG. 11C, in some examples, method 1400 may further comprise triggering the blocking, via a task engine, during a task period in which the task engine causes application of the task signal.

Although specific examples have been illustrated and described herein, a variety of alternate and/or equivalent implementations may be substituted for the specific examples shown and described without departing from the scope of the present disclosure. This application is intended to cover any adaptations or variations of the specific examples discussed herein.

The invention claimed is:

1. A device comprising:
a sensor signal input node;
a high-pass filter stage comprising:
an operational amplifier comprising an input node coupled to the sensor signal input node, and
a feedback integrator coupled between an output node of the operational amplifier and the input node of the operational amplifier to set a high-pass pole frequency of the high-pass filter stage; and
a multiplexer coupled been the sensor signal input mode and a plurality of electrode nodes, the multiplexer to selectively couple one of the plurality of electrode nodes to the sensor signal input node in response to an electrode selection signal.

2. The device of claim 1, further comprising:
a blanking switch coupled between the sensor signal input node and the input node of the operational amplifier.

3. The device of claim 1, wherein the high-pass filter stage further comprises an input common-mode feedback regulation operational transconductance amplifier (OTA) coupled to the input node of the operational amplifier.

4. The device of claim 1, wherein the feedback integrator comprises:
an input resistor coupled to the output node of the operational amplifier;
a feedback amplifier comprising an input node coupled to the input resistor;
a feedback capacitor coupled between the input node of the feedback amplifier and an output node of the feedback amplifier; and
an output capacitor coupled between the output node of the feedback amplifier and the input node of the operational amplifier.

5. The device of claim 4, wherein the input resistor comprises a pseudo resistor.

6. The device of claim 1, further comprising:
a first programmable gain amplifier stage comprising an input node coupled to the output node of the operational amplifier.

7. A device comprising:
a sensor signal input nodes;
a high-pass filter stage comprising:
an operational amplifier comprising an input coupled to the sensor signal input node, and
a feedback integrator coupled between an output node of the operational amplifier and the input node of the operational amplifier to set a high-pass pole frequency of the high-pass filter stage;
a first programmable gain amplifier stage comprising an input node coupled to the output node of the operational amplifier; and
a first bypass switch coupled between the input node of the first programmable gain amplifier stage and an output node of the first programmable gain amplifier stage.

8. The device of claim 7, further comprising:
a multiplexer coupled between the sensor signal input node and a plurality of electrode nodes, the multiplexer to selectively couple one of the plurality of electrode nodes to the sensor signal input node in response to an electrode selection signal.

9. The device of claim 7, further comprising:
a second programmable gain amplifier stage comprising an input node coupled to an output node of the first programmable gain amplifier stage.

10. The device of claim 9, further comprising:
a second bypass switch coupled between the input node of the second programmable gain amplifier stage and an output node of the second programmable gain amplifier stage.

11. The device of claim 9, further comprising:
an analog to digital converter coupled to an output node of the second programmable gain amplifier stage.

12. A device comprising:
a positive sensor signal input node;
a negative sensor signal input node; and
a high-pass filter stage comprising:
a fully differential operational amplifier comprising a first input node coupled to the positive sensor signal input node and a second input node coupled to the negative sensor signal input node, and
a common-mode feedback regulation operational transconductance amplifier (OTA) comprising a first input node coupled to the first input node of the fully differential operational amplifier, a second input node coupled to the second input node of the fully differential operational amplifier, a third input node coupled to a reference voltage node, and an output node coupled to the first input node and the second input node of the fully differential operational amplifier.

13. The device of claim 12, wherein the high-pass filter stage further comprises a feedback integrator coupled between a first output node and a second output node of the fully differential operational amplifier and the first input node and the second input node of the fully differential operational amplifier, respectively.

14. The device of claim 12, further comprising:
a first blanking switch coupled between the positive sensor signal input node and the first input node of the fully differential operational amplifier; and
a second blanking switch coupled between the negative sensor signal input node and the second input node of the fully differential operational amplifier.

15. The device of claim 14, further comprising:
a controller to selectively open the first blanking switch and the second blanking switch in response to a stimulation event to prevent saturation of the high-pass filter stage.

16. The device of claim 12, further comprising:
a first multiplexer coupled between the positive sensor signal input node and a plurality of electrode nodes, the first multiplexer to selectively couple one of the plurality of electrode nodes to the positive sensor signal input node in response to a first electrode selection signal; and
a second multiplexer coupled between the negative sensor signal input node and the plurality of electrode nodes, the second multiplexer to selectively couple another one of the plurality of electrode nodes to the negative sensor signal input node in response to a second electrode selection signal.

17. The device of claim 12, further comprising:
a first programmable gain differential amplifier stage comprising a first input node coupled to a first output node of the fully differential operational amplifier and a second input node coupled to a second output node of the fully differential operational amplifier.

18. The device of claim 17, further comprising:
a second programmable gain differential amplifier stage comprising a first input node coupled to a first output node of the first programmable gain differential amplifier stage and a second input node coupled to a second output node of the first programmable gain differential amplifier stage.

19. The device of claim 18, further comprising:

a differential analog to digital converter coupled to a first output node of the second programmable gain differential amplifier stage and a second output node of the second programmable gain differential amplifier stage.

20. A device comprising:

a high-pass filter amplifier stage comprising common mode rejection and offset correction;

a first programmable gain amplifier stage coupled to an output of the high-pass filter amplifier stage;

a first bypass switch coupled in parallel with the first programmable gain amplifier stage;

a second programmable gain amplifier stage coupled to an output of the first programmable gain amplifier stage;

a second bypass switch coupled in parallel with the second programmable gain amplifier stage;

an analog to digital converter coupled to an output of the second programmable gain amplifier stage; and a physiological sensor coupled to an input of the high-pass filter amplifier stage.

21. The device of claim 20, further comprising:

a blanking switch coupled between the physiological sensor and the input of the high-pass filter amplifier stage.

\* \* \* \* \*